(12) United States Patent
Sanghera et al.

(10) Patent No.: US 11,026,718 B2
(45) Date of Patent: Jun. 8, 2021

(54) DELIVERY SYSTEM FOR CARDIAC PACING

(71) Applicant: AtaCor Medical, Inc., San Clemente, CA (US)

(72) Inventors: Rick Sanghera, San Clemente, CA (US); Alan Marcovecchio, San Clemente, CA (US); Sean McGeehan, Rancho Santa Fe, CA (US)

(73) Assignee: ATACOR MEDICAL, INC., San Clemente, CA (US)

( * ) Notice: Subject to any disclaimer, the term of this patent is extended or adjusted under 35 U.S.C. 154(b) by 9 days.

(21) Appl. No.: 16/267,255

(22) Filed: Feb. 4, 2019

(65) Prior Publication Data

US 2019/0167981 A1   Jun. 6, 2019

Related U.S. Application Data

(63) Continuation of application No. 14/846,648, filed on Sep. 4, 2015, now Pat. No. 10,195,422.

(Continued)

(51) Int. Cl.
*A61N 1/05* (2006.01)
*A61N 1/365* (2006.01)
(Continued)

(52) U.S. Cl.
CPC ........ *A61B 17/3423* (2013.01); *A61N 1/0504* (2013.01); *A61N 1/0587* (2013.01);
(Continued)

(58) Field of Classification Search
CPC .... A61N 1/0592; A61N 1/362; A61N 1/0587; A61N 1/0504; A61N 1/37211;
(Continued)

(56) References Cited

U.S. PATENT DOCUMENTS

| 4,030,509 A | 6/1977 | Heilman |
| 4,146,037 A | 3/1979 | Flynn |

(Continued)

FOREIGN PATENT DOCUMENTS

| EP | 0668087 | 8/1995 |
| EP | 1530983 A2 | 5/2005 |

(Continued)

OTHER PUBLICATIONS

Brown, Charles G., et. al. 'Injuries Associated with Percutaneous Placement of Transthoracic Pacemakers.' Annals of Emergency Medicine 14.3 (1985): 223-28.

(Continued)

*Primary Examiner* — Mallika D Fairchild
(74) *Attorney, Agent, or Firm* — Pillsbury Winthrop Shaw Pittman LLP

(57) ABSTRACT

A delivery device for installing a medical device in a patient comprising a body portion having a proximal end and a distal end, the distal end having a chisel shaped tip, a receptacle disposed in the distal end of the body portion for receiving a medical device for implanting in the patient, a handle disposed at the proximal end of the body portion for facilitating advancement of the proximal end of the body portion into the patient.

20 Claims, 18 Drawing Sheets

Related U.S. Application Data

(60) Provisional application No. 62/146,569, filed on Apr. 13, 2015, provisional application No. 62/083,516, filed on Nov. 24, 2014, provisional application No. 62/045,683, filed on Sep. 4, 2014.

(51) Int. Cl.
    *A61N 1/375*     (2006.01)
    *A61B 17/34*     (2006.01)
    *A61N 1/362*     (2006.01)
    *A61N 1/372*     (2006.01)
    *A61M 25/00*     (2006.01)
    *A61M 25/06*     (2006.01)

(52) U.S. Cl.
CPC .......... *A61N 1/0592* (2013.01); *A61N 1/365* (2013.01); *A61N 1/3629* (2017.08); *A61N 1/3655* (2013.01); *A61N 1/36542* (2013.01); *A61N 1/36564* (2013.01); *A61N 1/37211* (2013.01); *A61B 17/3468* (2013.01); *A61B 2017/3427* (2013.01); *A61B 2017/3482* (2013.01); *A61B 2017/3488* (2013.01); *A61B 2017/3492* (2013.01); *A61M 25/00* (2013.01); *A61M 25/06* (2013.01); *A61M 2205/587* (2013.01); *A61N 1/059* (2013.01); *A61N 1/3752* (2013.01)

(58) Field of Classification Search
CPC .............. A61N 1/36564; A61N 1/3655; A61N 1/36542; A61N 1/365; A61N 1/059; A61N 1/3629; A61N 1/3752
See application file for complete search history.

(56) References Cited

U.S. PATENT DOCUMENTS

| | | |
|---|---|---|
| 4,270,549 A | 6/1981 | Heilman |
| 4,280,510 A | 7/1981 | ONeill |
| 4,291,707 A | 9/1981 | Heilman |
| 4,306,560 A | 12/1981 | Harris |
| 4,437,475 A | 3/1984 | White |
| 4,512,351 A | 4/1985 | Pohndorf |
| 4,532,931 A | 8/1985 | Mills |
| 4,538,624 A | 9/1985 | Tarjan |
| 4,636,199 A | 1/1987 | Victor |
| 4,765,341 A | 8/1988 | Mower |
| 4,787,389 A | 11/1988 | Tarjan |
| 4,832,687 A | 5/1989 | Smith, III |
| 4,846,191 A | 7/1989 | Brockway |
| 4,865,037 A | 9/1989 | Chin |
| 5,036,854 A | 8/1991 | Schollmeyer |
| 5,125,904 A | 6/1992 | Lee |
| 5,129,394 A | 7/1992 | Mehra |
| 5,176,135 A | 1/1993 | Fain |
| 5,203,348 A | 4/1993 | Dahl |
| 5,255,691 A | 10/1993 | Otten |
| 5,255,692 A | 10/1993 | Neubauer |
| 5,273,053 A | 12/1993 | Pohndorf |
| 5,300,106 A | 4/1994 | Dahl |
| 5,312,355 A | 5/1994 | Lee |
| 5,336,252 A | 8/1994 | Cohen |
| 5,364,361 A | 11/1994 | Battenfield |
| 5,391,156 A | 2/1995 | Hildwein |
| 5,441,504 A | 8/1995 | Pohndorf |
| 5,456,699 A | 10/1995 | Armstrong |
| 5,476,493 A | 12/1995 | Muff |
| 5,509,924 A | 4/1996 | Paspa |
| 5,534,018 A | 7/1996 | Wahlstrand |
| 5,545,205 A | 8/1996 | Schulte |
| 5,562,677 A | 10/1996 | Hildwein |
| 5,571,215 A | 11/1996 | Sterman |
| 5,613,953 A | 3/1997 | Pohndorf |
| 5,690,648 A | 11/1997 | Fogarty |
| 5,716,392 A | 2/1998 | Bourgeois |
| 5,728,151 A | 3/1998 | Garrison |
| 5,752,526 A | 5/1998 | Cosgrove |
| 5,776,110 A | 7/1998 | Guy |
| 5,814,076 A | 9/1998 | Brownlee |
| 5,823,946 A | 10/1998 | Chin |
| 5,871,532 A | 2/1999 | Schroeppel |
| 5,895,414 A | 4/1999 | Sanchez-Zambrano |
| 5,904,711 A | 5/1999 | Flom |
| 5,941,819 A | 8/1999 | Chin |
| 5,944,732 A | 8/1999 | Raulerson |
| 5,951,518 A | 9/1999 | Licata |
| 6,024,704 A | 2/2000 | Meador |
| 6,032,079 A | 2/2000 | KenKnight |
| 6,099,547 A | 8/2000 | Gellman |
| 6,104,957 A | 8/2000 | Alo |
| 6,122,552 A | 9/2000 | Tockman |
| 6,159,198 A | 12/2000 | Gardeski |
| 6,228,052 B1 | 5/2001 | Pohndorf |
| 6,283,127 B1 | 9/2001 | Sterman |
| 6,324,414 B1 | 11/2001 | Gibbons |
| 6,415,187 B1 | 7/2002 | Kuzma |
| 6,445,954 B1 | 9/2002 | Olive |
| 6,478,028 B1 | 11/2002 | Paolitto |
| 6,544,247 B1 | 4/2003 | Gardeski |
| 6,651,672 B2 | 11/2003 | Roth |
| 6,706,052 B1 | 3/2004 | Chin |
| 6,718,203 B2 | 4/2004 | Weiner |
| 6,721,597 B1 | 4/2004 | Bardy |
| 6,730,083 B2 | 5/2004 | Freigang |
| 6,733,500 B2 | 5/2004 | Kelley |
| 6,749,574 B2 | 6/2004 | OKeefe |
| 6,770,070 B1 | 8/2004 | Balbierz |
| 6,772,014 B2 | 8/2004 | Coe |
| 6,836,687 B2 | 12/2004 | Kelley |
| 6,866,044 B2 | 3/2005 | Bardy |
| 6,868,291 B1 | 3/2005 | Bonner |
| 6,887,229 B1 | 5/2005 | Kurth |
| 6,890,295 B2 | 5/2005 | Michels |
| 6,918,908 B2 | 7/2005 | Bonner |
| 6,999,819 B2 | 2/2006 | Swoyer |
| 7,033,326 B1 | 4/2006 | Pianca |
| 7,050,851 B2 | 5/2006 | Plombon |
| 7,069,083 B2 | 6/2006 | Finch |
| 7,096,064 B2 | 8/2006 | Deno |
| 7,117,039 B2 | 10/2006 | Manning |
| 7,120,496 B2 | 10/2006 | Bardy |
| 7,149,575 B2 | 12/2006 | Ostroff |
| 7,191,015 B2 | 3/2007 | Lamson |
| 7,195,637 B2 | 3/2007 | Mika |
| 7,218,970 B2 | 5/2007 | Ley |
| 7,229,450 B1 | 6/2007 | Chitre |
| 7,272,448 B1 | 9/2007 | Morgan |
| 7,288,096 B2 | 10/2007 | Chin |
| 7,316,667 B2 | 1/2008 | Lindstrom |
| 7,319,905 B1 | 1/2008 | Morgan |
| 7,322,960 B2 | 1/2008 | Yamamoto |
| 7,369,899 B2 | 5/2008 | Malinowski |
| 7,373,207 B2 | 5/2008 | Lattouf |
| 7,389,134 B1 | 6/2008 | Karicherla |
| 7,398,781 B1 | 7/2008 | Chin |
| 7,450,997 B1 | 11/2008 | Pianca |
| 7,499,758 B2 | 3/2009 | Cates |
| 7,515,969 B2 * | 4/2009 | Tockman .............. A61N 1/0587 607/122 |
| 7,539,542 B1 | 5/2009 | Malinowski |
| 7,627,375 B2 | 12/2009 | Bardy |
| 7,655,014 B2 | 2/2010 | Ko |
| 7,736,330 B2 | 6/2010 | Bardy |
| 7,751,885 B2 | 7/2010 | Bardy |
| 7,761,150 B2 | 7/2010 | Ghanem |
| 7,765,014 B2 | 7/2010 | Eversull |
| 7,801,622 B2 | 9/2010 | Camps |
| 7,837,671 B2 | 11/2010 | Eversull |
| 7,846,088 B2 | 12/2010 | Ness |
| 7,850,610 B2 | 12/2010 | Ferek-Petric |
| 7,890,191 B2 | 2/2011 | Rutten |
| 7,908,015 B2 | 3/2011 | Lazeroms |
| 7,930,028 B2 | 4/2011 | Lang |

(56) References Cited

U.S. PATENT DOCUMENTS

| | | |
|---|---|---|
| 7,930,040 B1 | 4/2011 | Kelsch |
| 7,967,833 B2 | 6/2011 | Sterman |
| 7,983,765 B1 | 7/2011 | Doan |
| 8,060,207 B2 | 11/2011 | Wallace |
| 8,065,020 B2 | 11/2011 | Ley |
| 8,066,702 B2 | 11/2011 | Rittman, III |
| 8,090,451 B2 | 1/2012 | Tyson, Jr. |
| 8,155,755 B2 | 4/2012 | Flynn |
| 8,157,813 B2 | 4/2012 | Ko |
| 8,260,436 B2 | 9/2012 | Gerber |
| 8,280,527 B2 | 10/2012 | Eckerdal |
| 8,332,036 B2 | 12/2012 | Hastings |
| 8,340,779 B2 | 12/2012 | Harris |
| 8,355,786 B2 | 1/2013 | Malinowski |
| 8,386,052 B2 | 2/2013 | Harris |
| 8,394,079 B2 | 3/2013 | Drake |
| 8,435,208 B2 | 5/2013 | Bardy |
| 8,442,620 B2 | 5/2013 | Silipo |
| 8,452,421 B2 | 5/2013 | Thenuwara |
| 8,457,742 B2 | 6/2013 | Jacobson |
| 8,478,424 B2 | 7/2013 | Tronnes |
| 8,478,426 B2 | 7/2013 | Barker |
| 8,478,431 B2 | 7/2013 | Griswold |
| 8,532,789 B2 | 9/2013 | Smits |
| 8,594,809 B2 | 11/2013 | Yang |
| 8,886,311 B2 | 11/2014 | Anderson |
| 9,622,778 B2 | 4/2017 | Wengreen |
| 9,636,505 B2 | 5/2017 | Sanghera |
| 9,707,389 B2 | 7/2017 | McGeehan |
| 10,130,824 B2 | 11/2018 | Grinberg |
| 10,137,295 B2 | 11/2018 | Marshall |
| 10,471,267 B2 | 11/2019 | Thompson-Nauman |
| 2002/0042629 A1 | 4/2002 | Bardy |
| 2002/0120294 A1 | 8/2002 | Kroll |
| 2003/0045904 A1 | 3/2003 | Bardy |
| 2003/0074041 A1 | 4/2003 | Parry |
| 2003/0088278 A1 | 5/2003 | Bardy |
| 2003/0114905 A1 | 6/2003 | Kuzma |
| 2003/0114906 A1 | 6/2003 | Booker |
| 2003/0114908 A1 | 6/2003 | Flach |
| 2003/0120264 A1 | 6/2003 | Lattouf |
| 2003/0130581 A1 | 7/2003 | Salo |
| 2003/0187458 A1 | 10/2003 | Carlson |
| 2004/0059348 A1 | 3/2004 | Geske |
| 2004/0088035 A1 | 5/2004 | W Guenst |
| 2004/0102829 A1 | 5/2004 | Bonner |
| 2004/0158185 A1 | 8/2004 | Moran |
| 2004/0210293 A1 | 10/2004 | Bardy |
| 2004/0215240 A1 | 10/2004 | Lovett |
| 2004/0230282 A1 | 11/2004 | Cates |
| 2004/0236396 A1 | 11/2004 | Coe |
| 2005/0027328 A1 | 2/2005 | Greenstein |
| 2005/0049663 A1 | 3/2005 | Harris |
| 2005/0131505 A1 | 6/2005 | Yokoyama |
| 2005/0165324 A1* | 7/2005 | Receveur ............... A61B 34/20 600/549 |
| 2005/0192639 A1 | 9/2005 | Bardy |
| 2005/0288731 A1 | 12/2005 | Shames |
| 2005/0288758 A1 | 12/2005 | Jones |
| 2006/0041295 A1 | 2/2006 | Osypka |
| 2006/0089699 A1 | 4/2006 | Imran |
| 2006/0116746 A1 | 6/2006 | Chin |
| 2006/0122676 A1 | 6/2006 | Ko |
| 2006/0129202 A1 | 6/2006 | Armstrong |
| 2006/0136004 A1 | 6/2006 | Cowan |
| 2006/0161205 A1 | 7/2006 | Mitrani |
| 2006/0241711 A1 | 10/2006 | Sathaye |
| 2006/0247672 A1 | 11/2006 | Vidlund |
| 2006/0247753 A1 | 11/2006 | Wenger |
| 2006/0253181 A1 | 11/2006 | Schulman |
| 2006/0266368 A1 | 11/2006 | Heintz |
| 2007/0023947 A1 | 2/2007 | Ludwig |
| 2007/0088394 A1 | 4/2007 | Jacobson |
| 2007/0100409 A1 | 5/2007 | Worley |
| 2007/0150015 A1 | 6/2007 | Zhang |
| 2007/0150023 A1 | 6/2007 | Ignagni |
| 2007/0179388 A1 | 8/2007 | Larik |
| 2007/0208402 A1 | 9/2007 | Helland |
| 2007/0249992 A1 | 10/2007 | Bardy |
| 2008/0046056 A1 | 2/2008 | OConnor |
| 2008/0103575 A1 | 5/2008 | Gerber |
| 2008/0183230 A1 | 7/2008 | Kemmetmueller |
| 2008/0243219 A1 | 10/2008 | Malinowski |
| 2008/0269716 A1 | 10/2008 | Bonde |
| 2008/0294217 A1 | 11/2008 | Lian |
| 2008/0300644 A1 | 12/2008 | Sathaye |
| 2009/0054947 A1 | 2/2009 | Bourn |
| 2009/0069803 A1 | 3/2009 | Starkebaum |
| 2009/0157091 A1 | 6/2009 | Buysman |
| 2009/0209970 A1 | 8/2009 | Tanaka |
| 2009/0222021 A1 | 9/2009 | Chang |
| 2009/0259283 A1 | 10/2009 | Brandt |
| 2009/0264780 A1 | 10/2009 | Schilling |
| 2009/0270962 A1 | 10/2009 | Yang |
| 2009/0326346 A1 | 12/2009 | Kracker |
| 2010/0016935 A1 | 1/2010 | Strandberg |
| 2010/0030227 A1 | 2/2010 | Kast |
| 2010/0030228 A1 | 2/2010 | Havel |
| 2010/0056858 A1 | 3/2010 | Mokelke |
| 2010/0082087 A1 | 4/2010 | Silipo |
| 2010/0094252 A1 | 4/2010 | Wengreen |
| 2010/0113963 A1 | 5/2010 | Smits |
| 2010/0125194 A1 | 5/2010 | Bonner |
| 2010/0137879 A1 | 6/2010 | Ko |
| 2010/0152747 A1 | 6/2010 | Padiy |
| 2010/0152798 A1 | 6/2010 | Sanghera |
| 2010/0185268 A1 | 7/2010 | Fowler |
| 2010/0211064 A1 | 8/2010 | Mahapatra |
| 2010/0217298 A1 | 8/2010 | Bardy |
| 2010/0217301 A1 | 8/2010 | Bardy |
| 2010/0241189 A1 | 9/2010 | Dobak |
| 2010/0305428 A1 | 12/2010 | Bonner |
| 2010/0318098 A1 | 12/2010 | Lund |
| 2010/0324579 A1 | 12/2010 | Bardy |
| 2011/0009933 A1 | 1/2011 | Barker |
| 2011/0024491 A1 | 2/2011 | Jamali |
| 2011/0066185 A1 | 3/2011 | Wotton, III |
| 2011/0077708 A1 | 3/2011 | Ostroff |
| 2011/0125163 A1 | 5/2011 | Rutten |
| 2011/0152706 A1 | 6/2011 | Christopherson |
| 2011/0178566 A1 | 7/2011 | Stahmann |
| 2011/0210156 A1 | 9/2011 | Smith |
| 2011/0224680 A1 | 9/2011 | Barker |
| 2011/0224681 A1 | 9/2011 | McDonald |
| 2011/0230906 A1 | 9/2011 | Modesitt |
| 2011/0257660 A1 | 10/2011 | Jones |
| 2012/0016377 A1 | 1/2012 | Geroy |
| 2012/0029335 A1 | 2/2012 | Sudam |
| 2012/0037291 A1 | 2/2012 | Goolishian |
| 2012/0078266 A1 | 3/2012 | Tyson |
| 2012/0089153 A1 | 4/2012 | Christopherson |
| 2012/0097174 A1 | 4/2012 | Spotnitz |
| 2012/0109250 A1 | 5/2012 | Cates |
| 2012/0123496 A1 | 5/2012 | Schotzko |
| 2012/0191106 A1 | 7/2012 | Ko |
| 2012/0209283 A1 | 8/2012 | Zhu |
| 2012/0209298 A1 | 8/2012 | McClurg |
| 2013/0006326 A1 | 1/2013 | Ackermann |
| 2013/0041345 A1 | 2/2013 | Kilcoin |
| 2013/0103049 A1 | 4/2013 | Bonde |
| 2013/0158564 A1 | 6/2013 | Harris |
| 2013/0178711 A1 | 7/2013 | Avneri |
| 2013/0226266 A1 | 8/2013 | Murtonen |
| 2013/0237781 A1 | 9/2013 | Gyrn |
| 2013/0238067 A1 | 9/2013 | Baudino |
| 2013/0296880 A1 | 11/2013 | Kelley |
| 2013/0338707 A1 | 12/2013 | Killion |
| 2014/0005755 A1 | 1/2014 | Wolf, II |
| 2014/0018872 A1 | 1/2014 | Siejko |
| 2014/0180273 A1 | 6/2014 | Nair |
| 2014/0257421 A1 | 9/2014 | Sanghera |
| 2014/0330208 A1 | 11/2014 | Christie |
| 2014/0330248 A1 | 11/2014 | Thompson-Nauman |
| 2014/0330287 A1 | 11/2014 | Thompson-Nauman |

(56) References Cited

U.S. PATENT DOCUMENTS

| | | |
|---|---|---|
| 2014/0330325 A1 | 11/2014 | Thompson-Nauman |
| 2014/0330326 A1 | 11/2014 | Thompson-Nauman |
| 2014/0330327 A1 | 11/2014 | Thompson-Nauman |
| 2014/0330328 A1 | 11/2014 | Christie |
| 2014/0330329 A1 | 11/2014 | Thompson-Nauman |
| 2014/0330331 A1 | 11/2014 | Thompson-Nauman |
| 2015/0013689 A1 | 1/2015 | Shackelford |
| 2015/0051612 A1 | 2/2015 | Schmidt |
| 2015/0051615 A1 | 2/2015 | Schmidt |
| 2015/0088155 A1 | 3/2015 | Stahmann |
| 2015/0133954 A1* | 5/2015 | Seifert ............... A61N 1/0563 606/129 |
| 2015/0142069 A1 | 5/2015 | Sambelashvili |
| 2015/0157497 A1 | 6/2015 | Hufford |
| 2015/0223906 A1 | 8/2015 | O'Neill |
| 2015/0313633 A1* | 11/2015 | Gross ............... A61B 1/00135 606/185 |
| 2015/0328473 A1 | 11/2015 | Bodner |
| 2016/0051159 A1 | 2/2016 | Mazaeva |
| 2016/0067478 A1 | 3/2016 | McGeehan |
| 2016/0067479 A1 | 3/2016 | Marcovecchio |
| 2016/0067480 A1 | 3/2016 | Sanghera |
| 2016/0067488 A1 | 3/2016 | Sanghera |
| 2016/0144192 A1 | 5/2016 | Sanghera |
| 2016/0175581 A1 | 6/2016 | Gordon |
| 2016/0184047 A1 | 6/2016 | Weir |
| 2017/0224995 A1 | 8/2017 | Sanghera |
| 2017/0304019 A1 | 10/2017 | Sanghera |
| 2017/0304634 A1 | 10/2017 | Sanghera |
| 2018/0021572 A1 | 1/2018 | McGeehan |
| 2018/0050199 A1 | 2/2018 | Sanghera |

FOREIGN PATENT DOCUMENTS

| | | |
|---|---|---|
| EP | 2346419 | 7/2011 |
| EP | 2967644 | 1/2016 |
| EP | 2994193 | 3/2016 |
| WO | 2002026315 A1 | 4/2002 |
| WO | 2006115772 A2 | 11/2006 |
| WO | 2013163267 A1 | 10/2013 |
| WO | 2015143327 | 9/2015 |

OTHER PUBLICATIONS

Brown, Charles G., et. al. 'Placement Accuracy of Percutaneous Transthoracic Pacemakers.' The American Journal of Emergency Medicine 3.3 (1985): 193-98.

Nagdev, Arun, and Daniel Mantuani. 'A Novel In-plane Technique for Ultrasound-guided Pericardiocentesis.' Tlie American Journal of Emergency Medicine 31.9 (2013): 1424.e6-1424.e9.

Jai, N. V., et. al. 'Relation of Internal Thoracic Artery to Lateral Sternal Border and Its Significance in Clinical Procedures.' International Journal of Biological & Medical Research 4.4 (2013): 3633-636.

PCT/US2017/041265; International Search Report and Written Opinion dated Sep. 25, 2017.

\* cited by examiner

700

702 — Determining, using one or more sensors, the location of blood-filled structures in the vicinity of an intercostal space associated with a cardiac notch of the left lung of a patient.

704 — Choosing a region for advancing of a lead through intercostal muscles associated with the cardiac notch of the patient, the region chosen based on the determined location of blood-filled structures, the lead configured to couple with a pulse generator for sensing intrinsic cardiac activity and for generating therapeutic electrical pulses for treating heart conditions in a patient.

706 — Advancing a lead through the intercostal muscles associated with the cardiac notch of the patient.

708 — Ceasing advancement of the lead in response to an indication, from one or more sensors, that the distal end of the lead is at the desired location.

FIG. 7

DELIVERY SYSTEM FOR CARDIAC PACING

CROSS-REFERENCE TO RELATED APPLICATIONS

This application is a continuation of and claims priority to and the benefit of U.S. patent application Ser. No. 14/846,648, titled Delivery System for Cardiac Pacing, filed Sep. 4, 2015, which claims priority to and the benefit of U.S. Provisional Patent Application No. 62/045,683, titled Cardiac Pacemaker System having Intracostal Electrodes, filed Sep. 4, 2014, U.S. Provisional Patent Application No. 62/083,516 titled Implantable Medical Device with Pacing Therapy, filed Nov. 24, 2014, and U.S. Provisional Patent Application No. 62/146,569 titled Delivery Systems and Implantable Leads for Intracostal Pacing, filed Apr. 13, 2015, the disclosures of each are incorporated herein by reference in their entirety.

TECHNICAL FIELD

The subject matter described herein relates to devices, systems and methods for cardiac pacing.

BACKGROUND

An artificial pacemaker is a medical device that helps control abnormal heart rhythms. A pacemaker uses electrical pulses to prompt the heart to beat at a normal rate. The pacemaker may speed up a slow heart rhythm, control a fast heart rhythm, and coordinate the chambers of the heart. The implantable portions of a pacemaker system generally comprise three main components: a pulse generator, one or more wires called leads, and electrodes found on each lead. The pulse generator produces the electrical signals that make the heart beat. Most pulse generators also have the capability to receive and respond to signals that are sent by the heart. Leads are insulated flexible wires that conduct electrical signals to the heart from the pulse generator. The leads may also relay signals from the heart to the pulse generator. One end of the lead is attached to the pulse generator and the electrode end of the lead is positioned on or in the heart.

SUMMARY

In one aspect, a delivery device for installing a medical device in a patient is described. The delivery device may comprise a body portion. The body portion may have a proximal end and a distal end. The distal end may have a chisel-shaped tip. The delivery device may have a receptacle disposed in the distal end of the body portion. The receptacle can be configured to receive a medical device for implanting into a patient with the medical device contained within the receptacle. A handle may be disposed at the proximal end of the body portion. The handle may be configured to facilitate advancement of the proximal end of the body portion into the patient.

In some variations, one or more of the following features may optionally be included in any feasible combination. The body portion may be configured to accommodate a port assembly contiguously attached to the medical device. The medical device may be a pulse generator. The delivery device may comprise a plunger configured to push the medical device out of the receptacle.

In another aspect a cardiac pacing system is described. The cardiac pacing system may comprise a pulse generator. The pulse generator may include a housing. The pulse generator may be configured to generate therapeutic electric pulses. The cardiac pacing system may comprise at least one lead receptacle. The at least one lead receptacle may be configured to be placed within an intercostal space of a patient. The cardiac pacing system may comprise at least one lead may be configured to electrically couple with the pulse generator and transmit the therapeutic electric pulses generated by the pulse generator. The at least one lead may comprise a lead body. The lead body may be configured to transmit the therapeutic electrical pulses between a distal end and a proximal end of the lead body. The at least one lead may comprise at least one accelerometer disposed at the distal end of the lead body. The at least one accelerometer may be configured to detect movement of the distal end of the lead as it is advanced into the patient.

In some variations, one or more of the following features may optionally be included in any feasible combination. The accelerometer may be configured to measure a pressure wave emitted by a blood-filled vessel of the patient.

In another aspect a cardiac pacing system is described. The cardiac pacing system may comprise a pulse generator. The pulse generator may include a housing. The pulse generator may be configured to generate therapeutic electric pulses. The cardiac pacing system may comprise at least one lead receptacle configured to be placed within an intercostal space of a patient. The cardiac pacing system may comprise at least one lead. The at least one lead may be configured to electrically couple with the pulse generator. The at least one lead may be configured to transmit the therapeutic electric pulses generated by the pulse generator. The at least one lead may comprise a lead body. The lead body may be configured to transmit the therapeutic electric pulses between a distal end and a proximal end of the lead body. The lead may comprise at least one sensor disposed at the distal end of the lead body. The at least one sensor may be configured to monitor physiological characteristics of the patient when the distal end of the lead is advanced through an intercostal space associated with a cardiac notch of the left lung of the patient.

In some variations, one or more of the following features may optionally be included in any feasible combination. The at least one sensor may comprises at least one accelerometer. The at least one accelerometer may be configured to detect movement of the distal end of the cardiac lead as it is advanced into the patient.

The at least one sensor may comprise a light source. The light source may be configured to emit photons having a wavelength that is readily absorbed by blood-filled structures. The at least one sensor may comprise a light detector. The light detector may be configured to detect photons reflected by tissue surrounding the blood-filled structures of the patient.

The at least one sensor may comprise a thermocouple configured to monitor the temperature of tissue in the vicinity of the distal end of the lead to facilitate a determination of the depth of the distal end of the lead in the patient. The at least one sensor may comprise a pH meter configured to monitor the pH level of tissue in the vicinity of the distal end of the lead to facilitate a determination of the depth of the distal end of the lead in the patient. The at least one sensor may comprise an electrical impedance sensor configured to monitor the level of electrical impedance of tissue in the vicinity of the distal end of the lead to facilitate a determination of the depth of the distal end of the lead in the patient.

In another aspect, a method of delivering a lead is disclosed. The method may comprise determining, using one or more sensors, the location of blood-filled structures in the vicinity of an intercostal space associated with a cardiac notch of the left lung of a patient. The method may comprise choosing a region for advancing a lead into intercostal muscles associated with the cardiac notch of the left lung of the patient, the region chosen based on the determined location of blood-filled structures, the lead configured to couple with a pulse generator for generating therapeutic electrical pulses for treating heart conditions in a patient. The method may comprise advancing the lead into the intercostal muscles associated with the cardiac notch of the left lung of the patient.

In some variations, one or more of the following features may optionally be included in any feasible combination. The method may comprise a light source configured to emit photons having a wavelength that is readily absorbed by blood-filled structures. The method may comprise a light detector configured to detect photons reflected by tissue surrounding the blood-filled structures of the patient. The light source and the light detector may be disposed at a distal tip of the lead.

The method may comprise ceasing advancing of the lead in response to a determination that a pH level measured by a pH sensor included at the distal tip of the lead matches a predetermined pH level of a desired location of the distal tip of the lead. The method may comprise ceasing advancing of the lead in response to a determination that a temperature measured by a temperature sensor included at the distal tip of the lead matches a predetermined temperature of a desired location of the distal tip of the lead.

In another aspect, a lead may be described. The lead may comprise a lead body having a distal end and a proximal end. The lead body may be configured to transmit electrical signals between the distal end and the proximal end. The proximal end may be configured to couple with a pulse generator for generating therapeutic electrical pulses for treating heart conditions in a patient. The lead may comprise an inflatable balloon disposed at the distal end of the lead body.

In some variations, one or more of the following features may optionally be included in any feasible combination. The inflatable balloon can be configured to be inflated to displace soft tissue elements of a patient during advancement of the distal end of the lead body through the patient. The inflatable balloon may be configured to be inflated to separate the distal end of the lead body from physiological elements of the patient.

The balloon may facilitate avoidance of perforation of physiological elements of the patient by the distal end of the lead body.

The inflatable balloon may be configured to inflate transversely from the lead body to displace the lead body from physiological elements of the patient. The inflatable balloon may be disposed on the sides of the lead body. The inflatable balloon may be disposed circumferentially around the lead body.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes, it should be readily understood that such features are not intended to be limiting. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 7 is an illustration of an exemplary process flow illustrating a method of placing a pacing lead having features consistent with the current subject matter;

When practical, similar reference numbers denote similar structures, features, or elements.

DETAILED DESCRIPTION

Implantable medical devices (IMDs), such as cardiac pacemakers or implantable cardioverter defibrillators (ICDs), provide therapeutic electrical stimulation to the heart of a patient. This electrical stimulation may be delivered via electrodes on one or more implantable endocardial or epicardial leads that are positioned in or on the heart. This electrical stimulation may also be delivered using a leadless cardiac pacemaker disposed within a chamber of the heart. Therapeutic electrical stimulation may be delivered to the heart in the form of electrical pulses or shocks for pacing, cardioversion or defibrillation.

An implantable cardiac pacemaker may be configured to facilitate the treatment of cardiac arrhythmias. The devices, systems and methods of the present disclosure may be used to treat cardiac arrhythmias including, but not limited to, bradycardia, tachycardia, atrial flutter and atrial fibrillation. Resynchronization pacing therapy may also be provided.

A cardiac pacemaker consistent with the present disclosure may include a pulse generator implanted adjacent the rib cage of the patient, for example, on the ribcage under the pectoral muscles, laterally on the ribcage, within the mediastinum, subcutaneously on the sternum of the ribcage, and the like. One or more leads may be connected to the pulse generator. A lead may be inserted, for example, between two ribs of a patient so that the distal end of the lead is positioned within the mediastinum of the patient adjacent, but not touching, the heart. The distal end of the lead may include an electrode for providing electrical pulse therapy to the patient's heart and may also include at least one sensor for detecting a state of the patient's organs and/or systems. The cardiac pacemaker may include a unitary design where the components of the pulse generator and lead are incorporated within a single form factor. For example, where a first portion of the unitary device resides within the subcutaneous tissue and a second portion of the unitary device is placed through an intercostal space into a location within the mediastinum.

Figure 1:
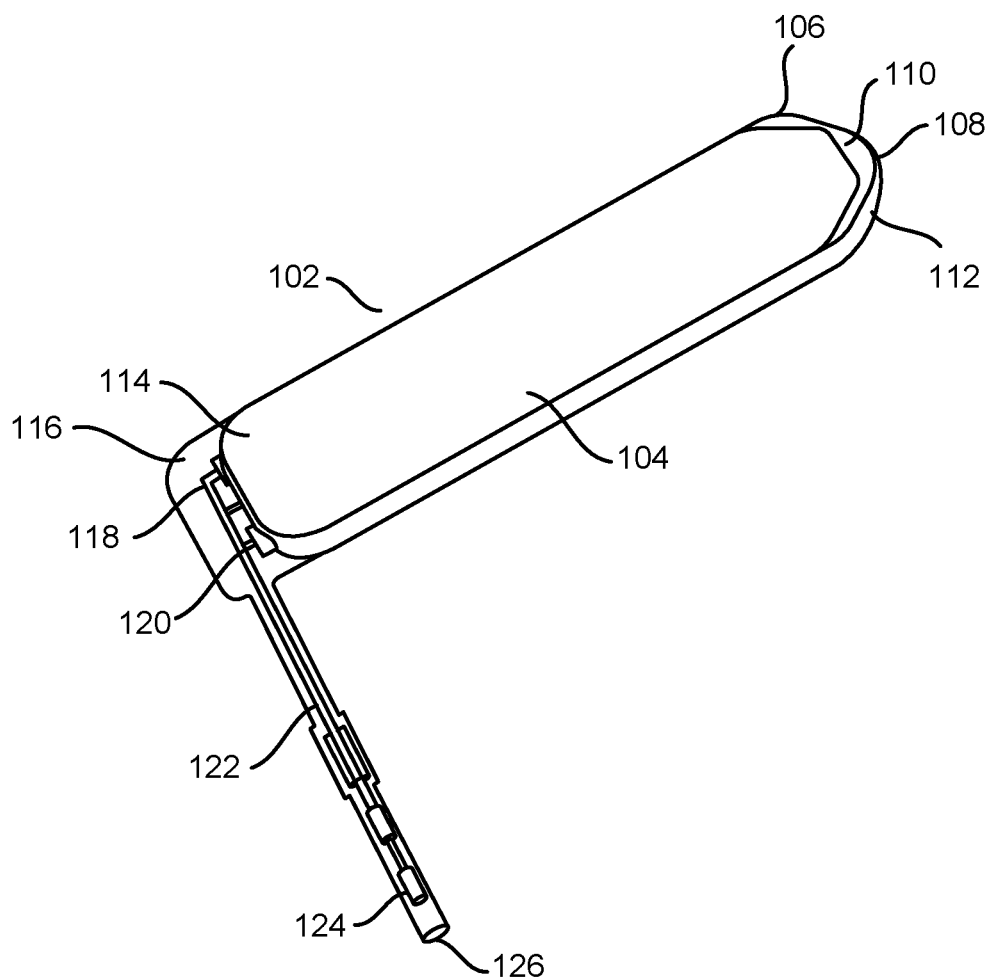
FIG. 1 is a front-view of an exemplary pulse generator having features consistent with implementations of the current subject matter.

FIG. 1 is a front-view 100 of a pulse generator 102 having features consistent with implementations of the current subject matter. The pulse generator 102 may be referred to as a cardiac pacemaker. The pulse generator 102 can include a housing 104, which may be hermetically sealed. In the present disclosure, and commonly in the art, housing 104 and everything within it may be referred to as a pulse generator, despite there being elements inside the housing other than those that generate pulses (for example, processors, storage, battery, etc.).

Housing 104 can be substantially rectangular in shape and the first end of the housing 104 may include a tapered portion 108. The tapered portion can include a first tapered edge 110, tapered inwardly toward the transverse plane. The tapered portion 108 can include a second tapered edge 112 tapered inwardly toward the longitudinal plane. Each of the first tapered edge 110 and the second tapered edge 112 may have a similar tapered edge generally symmetrically disposed on the opposite side of tapered portion 108, to form two pairs of tapered edges. The pairs of tapered edges may thereby form a chisel-shape at the first end 106 of pulse generator 102. When used in the present disclosure, the term "chisel-shape" refers to any configuration of a portion of housing 104 that facilitates the separation of tissue planes during placement of pulse generator 102 into a patient. The "chisel-shape" can facilitate creation of a tightly fitting and properly sized pocket in the patient's tissue in which the pulse generator may be secured. For example, a chisel-shape portion of housing 104 may have a single tapered edge, a pair of tapered edges, 2 pairs of tapered edges, and the like. Generally, the tapering of the edges forms the shape of a chisel or the shape of the head of a flat head screwdriver. In some variations, the second end 114 of the pulse generator can be tapered. In other variations, one or more additional sides of the pulse generator 102 can be tapered.

Housing 104 of pulse generator 102 can include a second end 114. The second end 114 can include a port assembly 116. Port assembly 116 can be integrated with housing 104 to form a hermetically sealed structure. Port assembly 116 may be configured to facilitate the egress of conductors from housing 104 of pulse generator 102 while maintaining a seal. For example, port assembly 116 may be configured to facilitate the egress of a first conductor 118 and a second conductor 120 from housing 104. The first conductor 118 and the second conductor 120 may combine within port assembly 116 to form a twin-lead cable 122. In some variations, the twin-lead cable 122 can be a coaxial cable. The twin-lead cable 122 may include a connection port 124 remote from housing 104. Connection port 124 can be configured to receive at least one lead, for example, a pacing lead. Connection port 124 of the cable 122 can include a sealed housing 126. Sealed housing 126 can be configured to envelope a portion of the received lead(s) and form a sealed connection with the received lead(s).

Port assembly 116 may be made from a different material than housing 104. For example, housing 104 may be made from a metal alloy and port assembly 116 may be made from a more flexible polymer. While port assembly 116 may be manufactured separately from housing 104 and then integrated with it, port assembly 116 may also be designed to be part of housing 104 itself. The port assembly 116 may be externalized from the housing 104 as depicted in FIG. 1. The port assembly 116 may be incorporated within the shape of housing 104 of pulse generator 102.

Figure 2:
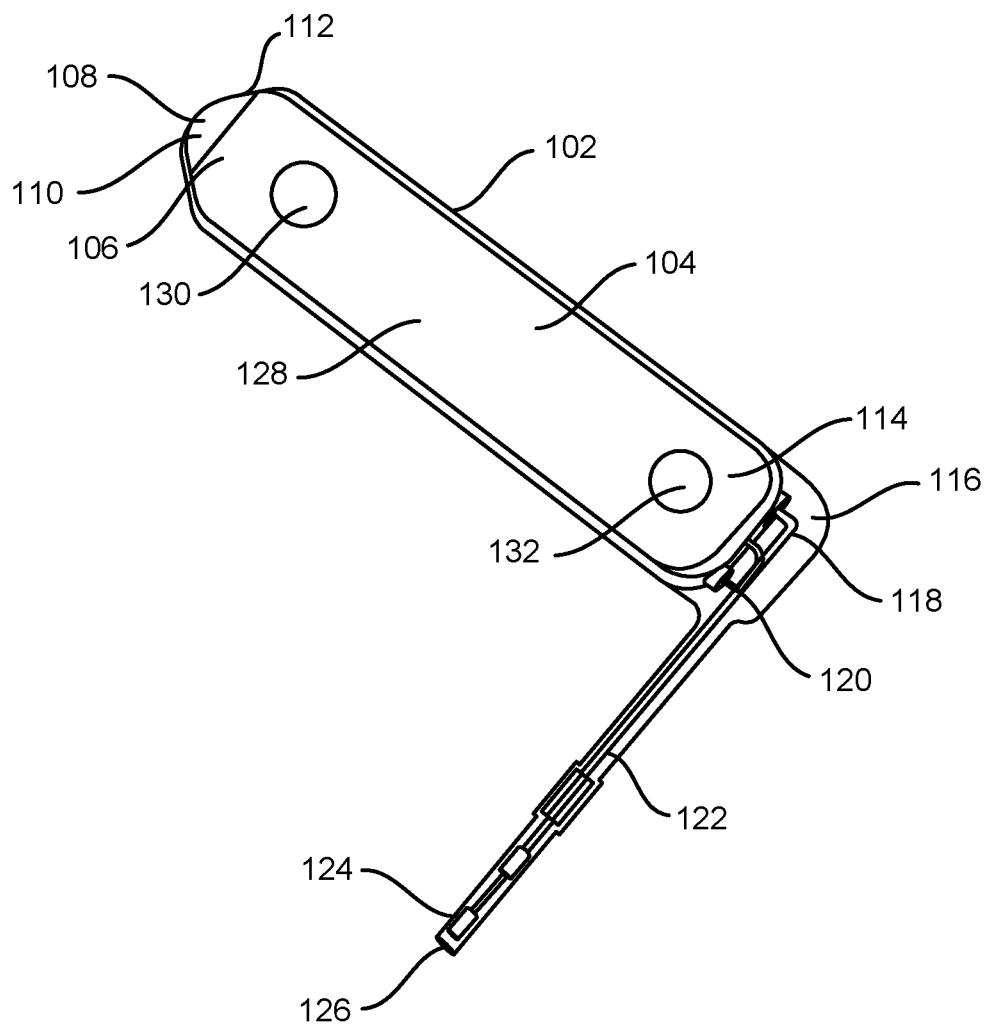
FIG. 2 is a rear-view of an exemplary pulse generator having features consistent with implementations of the current subject matter.

FIG. 2 is a rear-view 200 of pulse generator 102 showing the back-side 128 of housing 104. As shown, pulse generator 102 can include one or more electrodes or sensors disposed within housing 104. As depicted in the example of FIG. 2, housing 104 includes a first in-housing electrode 130 and a second in-housing electrode 132. The various electrodes illustrated and discussed herein may be used for delivering therapy to the patient, sensing a condition of the patient, and/or a combination thereof. A pulse generator consistent with the present disclosure installed at or near the sternum of a patient can monitor the heart, lungs, major blood vessels, and the like through sensor(s) integrated into housing 104.

Figure 3:
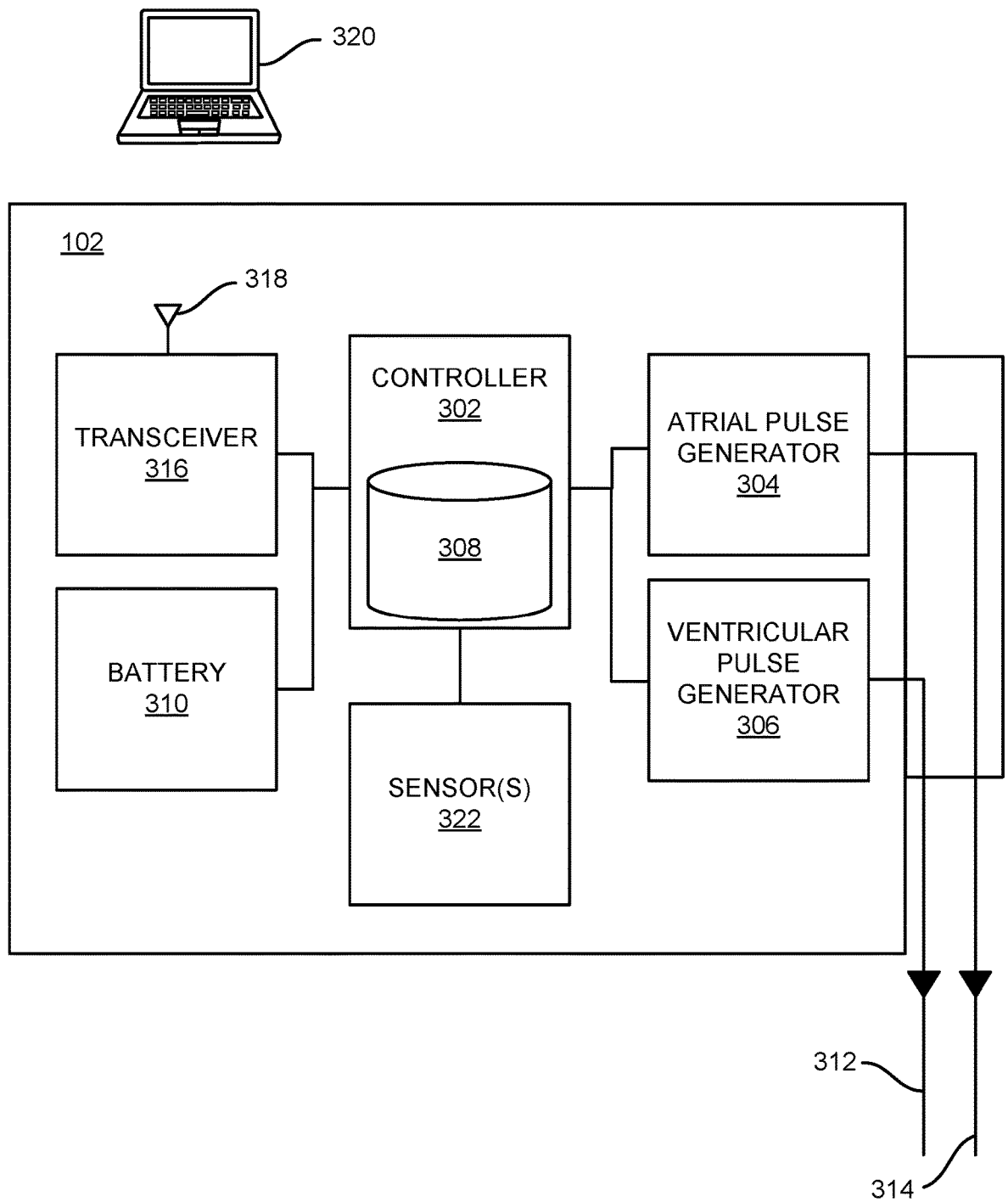
FIG. 3 is an illustration of a simplified schematic diagram of an exemplary pulse generator having features consistent with implementations of the current subject matter.

FIG. 3 is an illustration 300 of a simplified schematic diagram of an exemplary pulse generator 102 having features consistent with the current subject matter. Pulse generator 102 can include signal processing and therapy circuitry to detect various cardiac conditions. Cardiac conditions can include ventricular dyssynchrony, arrhythmias such as bradycardia and tachycardia conditions, and the like. Pulse generator 102 can be configured to sense and discriminate atrial and ventricular activity and then deliver appropriate electrical stimuli to the heart based on a sensed state of the heart.

Pulse generator 102 can include one or more components. The one or more components may be hermetically sealed within the housing 104 of pulse generator 102. Pulse generator 102 can include a controller 302, configured to control the operation of the pulse generator 102. The pulse generator 102 can include an atrial pulse generator 304 and may also include a ventricular pulse generator 306. Controller 302 can be configured to cause the atrial pulse generator 304 and the ventricular pulse generator 306 to generate electrical pulses in accordance with one or more protocols that may be loaded onto controller 302. Controller 302 can be configured to control pulse generators 304, 306, to deliver electrical pulses with the amplitudes, pulse widths, frequency, or electrode polarities specified by the therapy protocols, to one or more atria or ventricles.

Controller electronic storage 308 can store instructions configured to be implemented by the controller to control the functions of pulse generator 102.

Controller 302 can include a processor(s). The processor(s) can include any one or more of a microprocessor, a controller, a digital signal processor (DSP), an application specific integrated circuit (ASIC), a field-programmable gate array (FPGA), or equivalent discrete or analog logic circuitry. The functions attributed to controller 302 herein may be embodied as software, firmware, hardware or any combination thereof.

The pulse generator 102 can include a battery 310 to power the components of the pulse generator 102. In some variations, battery 310 can be configured to charge a capacitor. Atrial pulse generator 304 and ventricular pulse generator 306 can include a capacitor charged by the battery 310. The electrical energy stored in the capacitor(s) can be discharged as controlled by controller 302. The electrical energy can be transmitted to its destination through one or more electrode leads 312, 314. The leads can include a ventricular pulsing lead 312, an atrial pulsing lead 314, and/or other leads.

Pulse generator 102 can include one or more sensors 322. Sensor(s) 322 can be configured to monitor various aspects of a patient's physiology. Sensor(s) 322 may be embedded in the housing of pulse generator 102, incorporated into leads 312, 314 or be incorporated into separate leads. Sensors 322 of pulse generator 102 can be configured to detect, for example, signals from a patient's heart. The signals can be decoded by controller 302 of the pulse generator to determine a state of the patient. In response to detecting a cardiac arrhythmia, controller 302 can be configured to cause appropriate electrical stimulation to be transmitted through electrodes 312 and 314 by atrial pulse generator 304 and/or ventricular pulse generator 306.

Sensor(s) 322 can be further configured to detect other physiological states of the patient, for example, a respiration rate, blood oximetry, and/or other physiological states. In variations where the pulse generator 102 utilizes a plurality of electrodes, controller 302 may be configured to alter the sensing and delivery vectors between available electrodes to enhance the sensitivity and specificity of arrhythmia detection and improve efficacy of the therapy delivered by the electrical impulses from the pulse generator 102.

Pulse generator 102 can include a transceiver 316. The transceiver can include an antenna 318. The transceiver 316 can be configured to transmit and/or receive radio frequency signals. The transceiver 316 can be configured to transmit and/or receive wireless signals having any wireless communication protocol. Wireless communication protocols can include Bluetooth, Bluetooth low energy, Near-Field Communication, WiFi, and/or other radio frequency protocols.

The transceiver 316 can be configured to transmit and/or receive radio frequency signals to and/or from a programmer 320. The programmer 320 can be a computing device external to the patient. Programmer 320 may comprise a transceiver configured to transmit and/or receive radio frequency signals to and/or from the transceiver 316 of the pulse generator 102. Transceiver 316 can be configured to wirelessly communicate with programmer 320 through induction, radio-frequency communication or other short-range communication methodologies.

In some variations, programmer 320 can be configured to communicate with the pulse generator 102 through longer-range remote connectivity systems. Such longer-range remote connectivity systems can facilitate remote access, by an operator, to pulse generator 102 without the operator being in close proximity with the patient. Longer-range remote connectivity systems can include, for example, remote connectivity through the Internet, and the like. When an operator connects with pulse generator 102 through longer-range remote connectivity systems, a local device can be positioned within a threshold distance of the patient. The local device can communicate using one or more radio-frequency wireless connections with the pulse generator 102. The local device can, in turn, include hardware and/or software features configured to facilitate communication between it and an operator device at which the operator is stationed. The local device can be, for example, a mobile computing device such as a smartphone, tablet, laptop, and the like. The local device can be a purpose-built local device configured to communicate with the pulse generator 102. The local device can be paired with the pulse generator 102 such that the communications between the pulse generator 102 and the local device are encrypted. Communications between the local device and the operator device can be encrypted.

Programmer 320 can be configured to program one or more parameters of the pulse generator 102. The parameter(s) can include timing of the stimulation pulses of the atrial pulse generator, timing of the stimulation pulses of the ventricular pulse generator, timing of pulses relative to certain sensed activity of the anatomy of the patient, the energy levels of the stimulation pulses, the duration of the stimulation pulses, the pattern of the stimulation pulses and other parameters. The programmer 320 can facilitate the performance of diagnostics on the patient or the pulse generator 102.

Programmer 320 can be configured to facilitate an operator of the programmer 320 to define how the pulse generator 102 senses electrical signals, for example ECGs, and the like. The programmer 320 can facilitate an operator of the programmer 320 to define how the pulse generator 102 detects cardiac conditions, for example ventricular dyssynchrony, arrhythmias, and the like. The programmer 320 can facilitate defining how the pulse generator 102 delivers therapy, and communicates with other devices.

An operator can fine-tune parameters through the programmer 320. For example, the sensitivity of sensors embodied in the housing of the pulse generator 302, or within leads, can be modified. Programmer 320 can facilitate setting up communication protocols between the pulse generator 102 and another device such as a mobile computing device. Programmer 320 can be configured to facilitate modification of the communication protocols of the pulse generator 102, such as adding security layers, or preventing two-way communication. Programmer 320 can be configured to facilitate determination of which combination of implanted electrodes are best suited for sensing and therapy delivery.

Programmer 320 can be used during the implant procedure. For example, programmer 320 can be used to determine if an implanted lead is positioned such that acceptable performance will be possible. If the performance of the system is deemed unacceptable by programmer 320, the lead may be repositioned by the physician, or an automated delivery system, until the lead resides in a suitable position. Programmer 320 can also be used to communicate feedback from sensors disposed on the leads and housing 104 during the implant procedure.

In some cases, concomitant devices such as another pacemaker, an ICD, or a cutaneous or implantable cardiac monitor, can be present in a patient, along with pulse generator 102. Pulse generator 102 can be configured to communicate with such concomitant devices through transceiver 316 wirelessly, or the concomitant device may be physically connected to pulse generator 102. Physical connection between devices may be accomplished using a lead emanating from pulse generator 102 that is compatible with the concomitant device. For example, the distal end of a lead emanating from pulse generator 102 may be physically and electrically connected to a port contained on the concomitant device. Physical connection between devices may also be accomplished using an implantable adaptor that facilitates electrical connection between the lead emanating from pulse generator 102 and the concomitant device. For example, an adapter may be used that will physically and electrically couple the devices despite not having native components to facilitate such connection. Concomitant devices may be connected using a "smart adapter" that provides electrical connection between concomitant devices and contains signal processing capabilities to convert signal attributes from each respective device such that the concomitant devices are functionally compatible with each other.

Pulse generator 102 can be configured to have a two-way conversation or a one-way conversation with a concomitant device. Controller 302 can be configured to cause the concomitant device to act in concert with pulse generator 102 when providing therapy to the patient, or controller 302 can gather information about the patient from the concomitant device.

In some variations, pulse generator 102 can be configured to be triggered via one-way communication from a concomitant device to pulse generator 102.

Figure 4A:
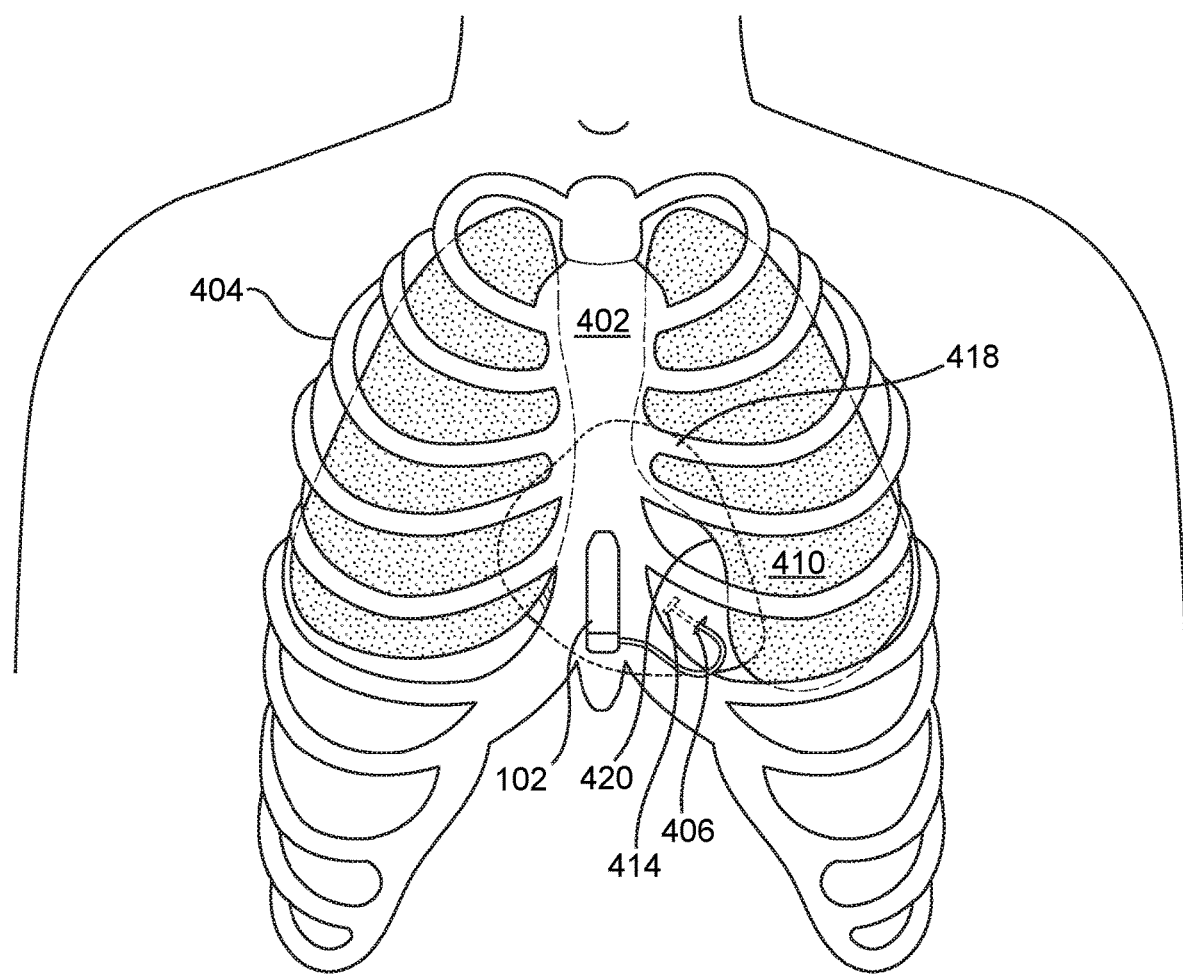
FIG. 4A is an illustration showing exemplary placements of elements of a cardiac pacing system having features consistent with the current subject matter.
Figure 4B:
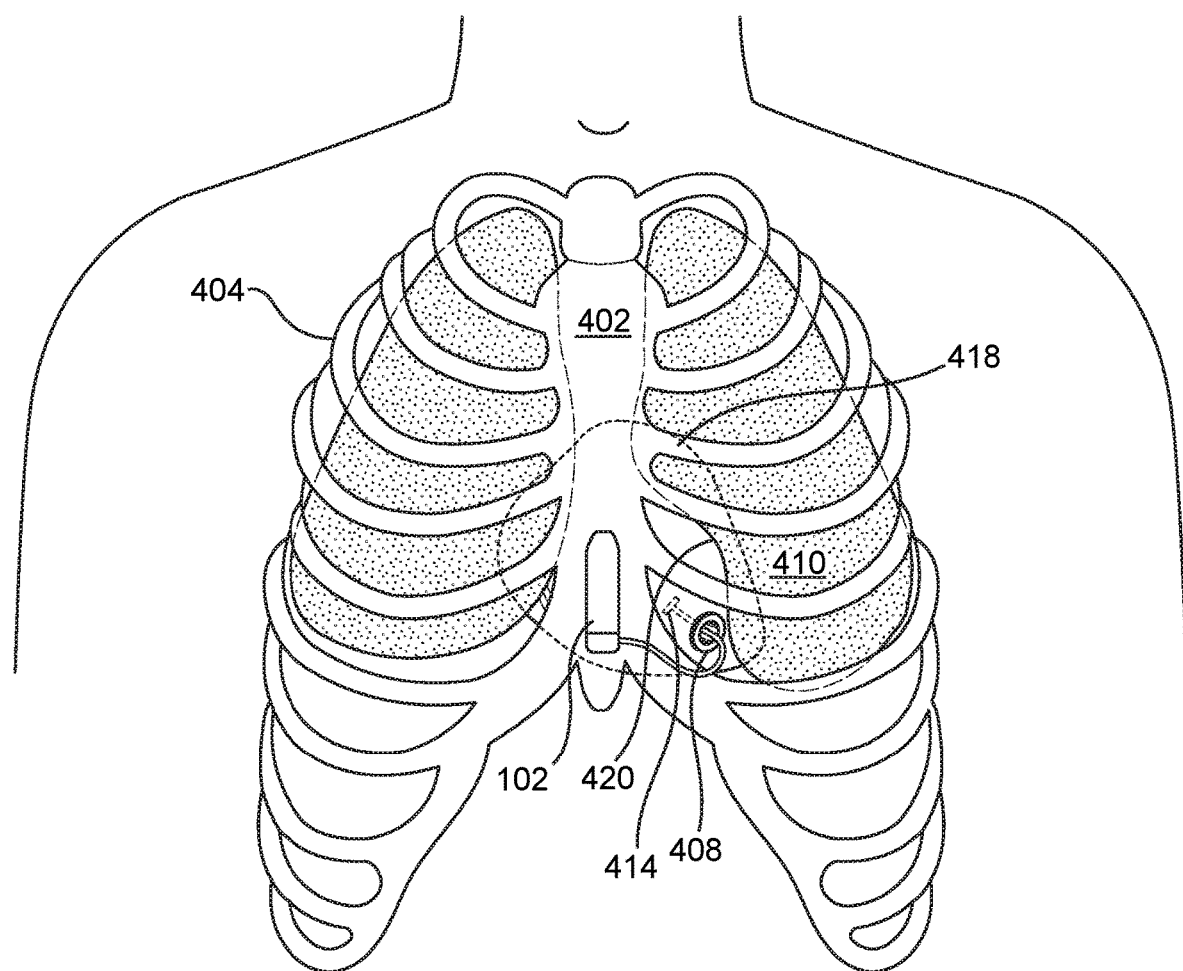
FIG. 4B is an illustration showing exemplary placements of elements of a cardiac pacing system having features consistent with the current subject matter.

FIGS. 4A and 4B are illustrations showing exemplary placements of elements of a cardiac pacing system having features consistent with the present disclosure. Pulse generator 102 can be disposed in a patient, adjacent an outer surface of ribcage 404. For example, pulse generator 102 can be disposed on the sternum 402 of the patient's ribcage 404. A lead 414, attached to pulse generator 102, may also be disposed in the patient by traversing through intercostal muscle 410 of the patient. Lead 414 may optionally pass through a receptacle 408 in intercostal muscle 410 to guide the lead, fix the lead, and/or electrically insulate the lead from the tissue of the intercostal muscle 410 (examples of such receptacles are described herein with respect to FIGS. 13-16).

In other variations, pulse generator 102 can be disposed outside of a patient's ribcage in a pectoral position, outside of the patient's ribcage in a lateral position, below (inferior to) the patient's ribcage in a subxiphoid or abdominal position, within the patient's mediastinum, or the like.

Lead 414 may be passed through the ribcage so the distal end of the lead and its electrodes are disposed on, or pass through, the inner surface of the rib or inner surface of the innermost intercostal muscle, or may alternatively traverse further within the thoracic cavity, but without physically contacting the tissue comprising the heart. This placement may be referred to herein as intracostal or intracostally.

Leads may be inserted between any two ribs within the thoracic cavity, for example, as shown in FIG. 4A. In some variations, it is desirable to insert the lead through one of the intercostal spaces associated with cardiac notch of the left lung 420. For example, between the fourth and fifth ribs or between the fifth and sixth ribs. Due to variations in anatomy, the rib spacing associated with the cardiac notch of the left lung 420 may differ. In some patients the cardiac notch of the left lung 420 may not be present or other cardiac anomalies such as dextrocardia may require the insertion through alternative rib spaces. Lead 414 may be inserted into such a location through an incision 406, as shown in FIG. 4A. Lead 414 may optionally be inserted into such a location through a receptacle 408, as shown in FIG. 4B.

Figure 4C:
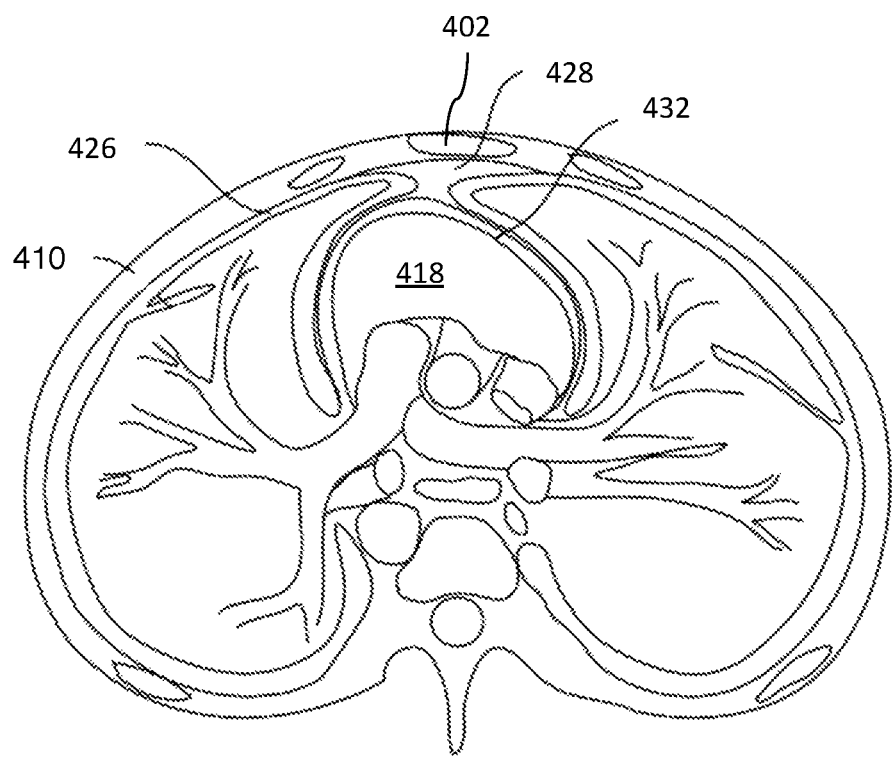
FIG. 4C is a cross-sectional illustration of a thoracic region of a patient.

Precise placement of a distal end of lead 414, which may include electrode(s) for pacing or sensing, is now described further with reference to the anatomical illustrations of FIGS. 4A, 4B and 4C. In some variations, the distal end of lead 414 can be located within the intercostal space or intercostal muscle 410. In such variations, the distal end of lead 414 is preferably surrounded by a receptacle 408 that electrically insulates the distal end of the lead 414 from the intercostal muscle 410. In another variation, the distal end of lead 414 may be placed just on the inner surface of a rib or on the inner surface of the innermost intercostal muscle.

The distal end of lead 414 can also be positioned so as to abut the parietal pleura of the lung 426. In other variations, the distal end of lead 414 can be positioned so as to terminate within the mediastinum 428 of the thoracic cavity of the patient, proximate the heart 418, but not physically in contact with the heart 418 or the pericardium 432 of heart 418. Alternatively, the distal end of lead 414 can be placed to abut the pericardium 432, but not physically attach to the epicardial tissue comprising the heart.

The distal end of lead 414 may be physically affixed to cartilage or bone found within the thoracic cavity, for example, to a rib, to cartilage of a rib, or to other bone or cartilage structure in the thoracic cavity. In one variation, the lead can be disposed such that it is wrapped around the patient's sternum 402.

For certain placements, lead 414 can be adequately fixed by direct physical contact with surrounding tissue. In other variations, an additional fixation mechanism may be used. For example, the distal end of lead 414 can incorporate a fixation mechanism such as a tine, hook, spring, screw, or other fixation device. The fixation mechanism can be configured to secure the lead in the surrounding tissue, cartilage, bone, or other tissue, to prevent the lead from migrating from its original implantation location.

Figure 5:
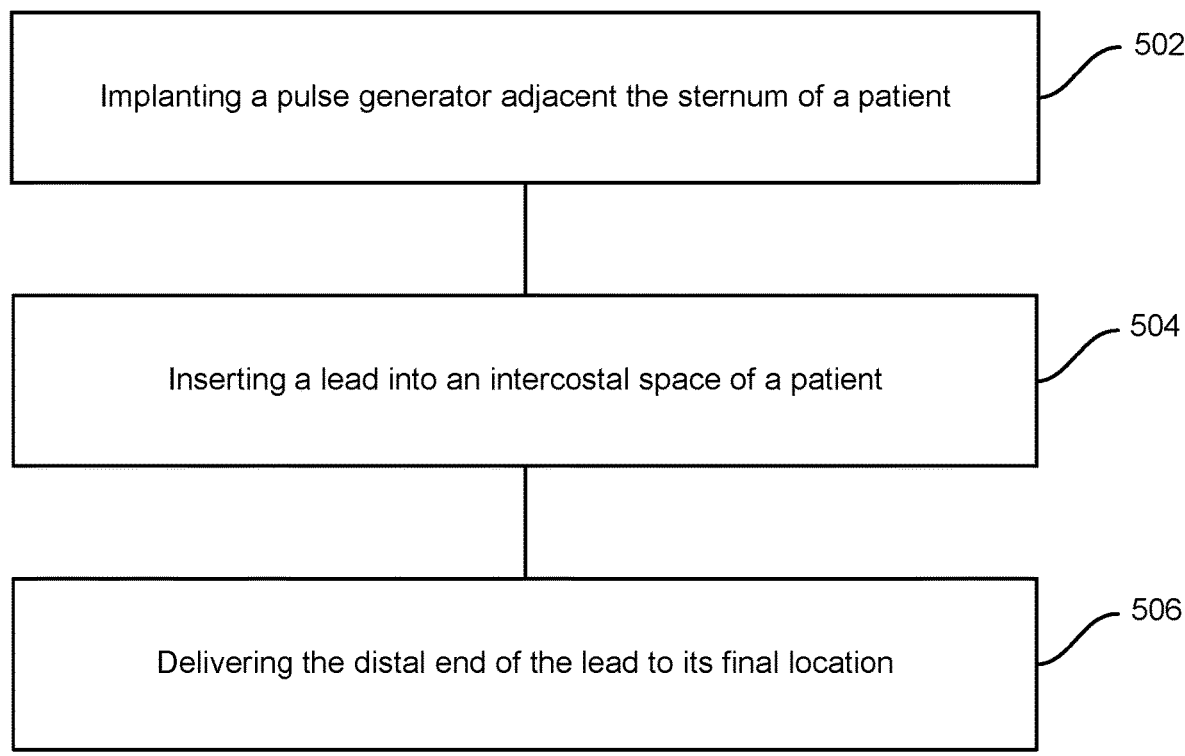
FIG. 5 is an illustration of an exemplary method of implanting a cardiac pacing system into a patient having features consistent with the current subject matter.

FIG. 5 is an illustration 500 of an exemplary method of implanting a cardiac pacing system into a patient consistent with the present disclosure. At 502, a pulse generator 102 may be implanted, in a manner described above, adjacent the sternum 402 of a patient. Optionally, pulse generator 102 may be at least partially chisel-shaped to facilitate implantation and the separation of tissue planes. At 504, a lead 414 may be inserted into an intercostal space 410 of a patient. As described above, lead 414 may optionally be inserted into a receptacle 408 disposed within intercostal space 410. At 506, the distal end of lead 414 is delivered to one of a number of suitable final locations for pacing, as described above.

Figure 6A:
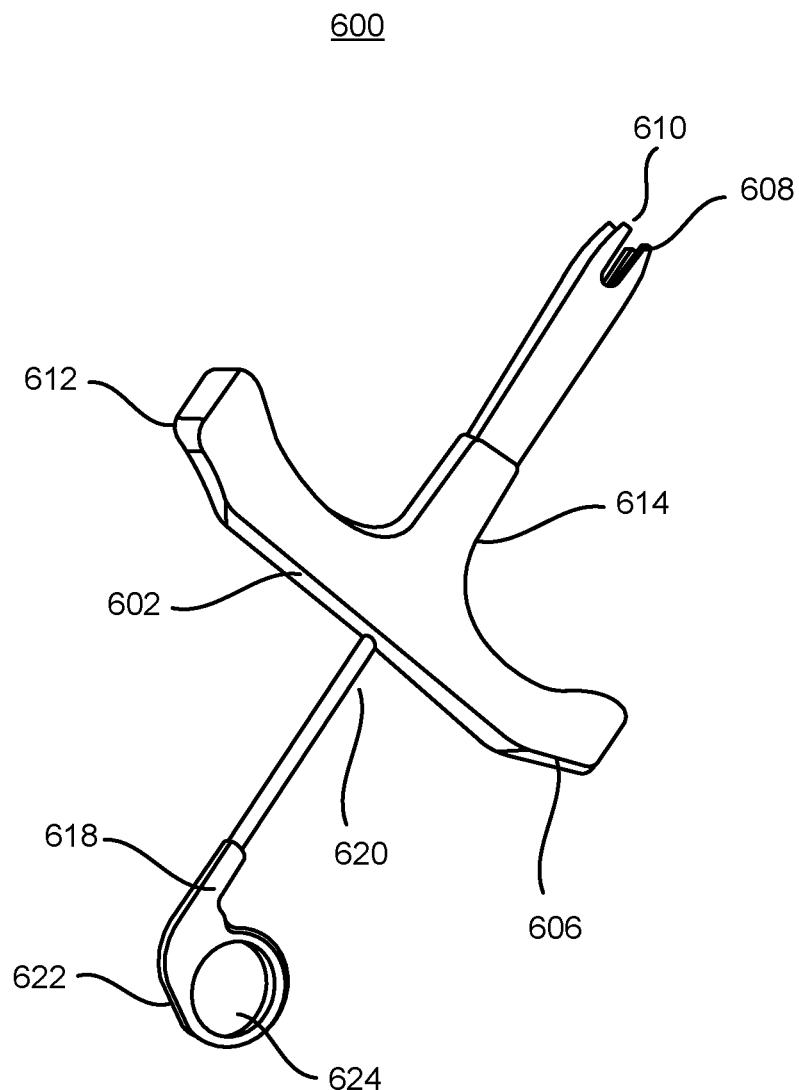
FIG. 6A is an illustration of an exemplary delivery system for a pulse generator having features consistent with implementations of the current subject matter.
Figure 6B:
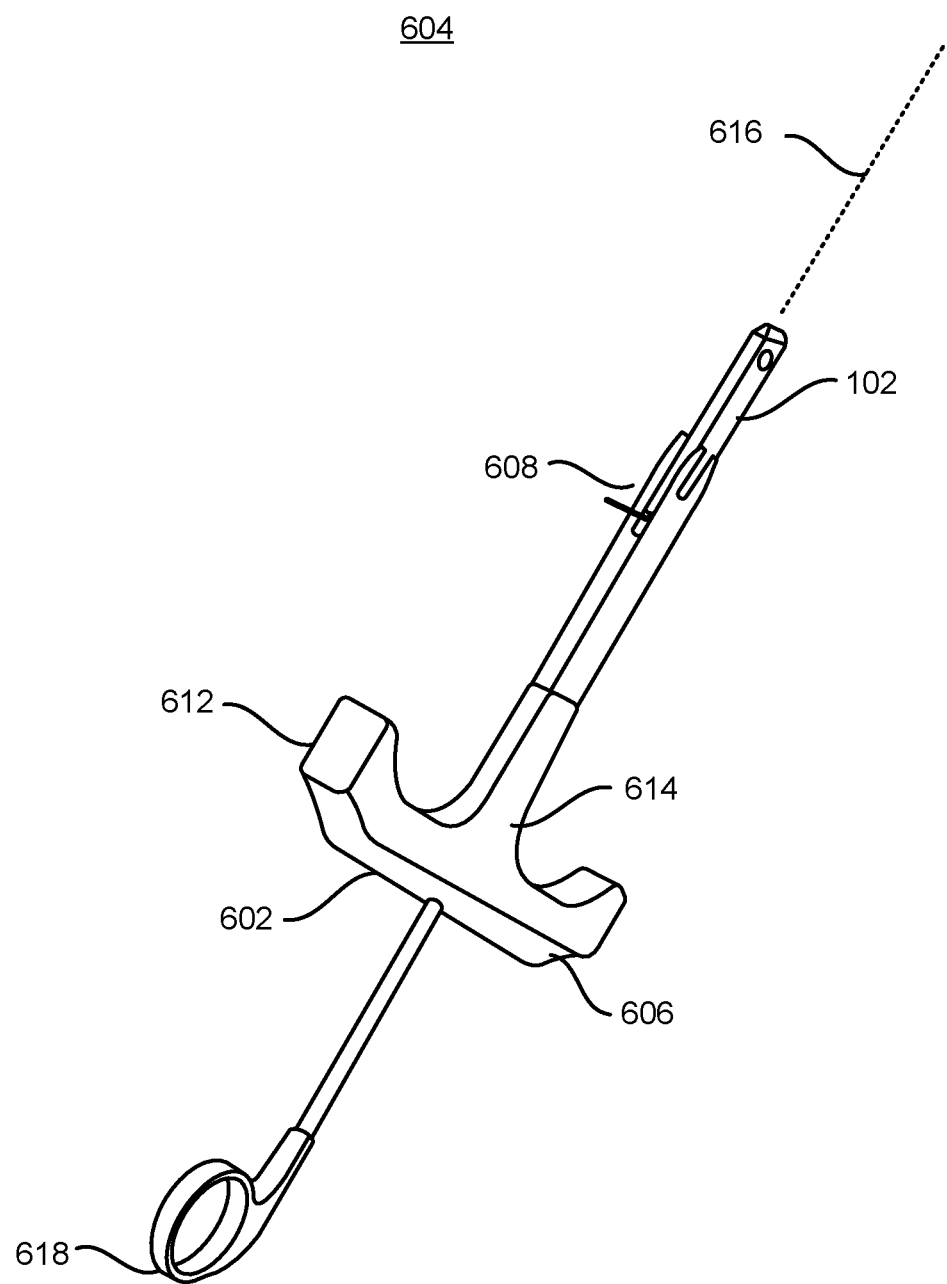
FIG. 6B is an illustration of an exemplary delivery system with a pulse generator disposed therein consistent with implementations of the current subject matter.

FIG. 6A is an illustration 600 of a pulse generator delivery system 602 for facilitating positioning of pulse generator 102 into a patient, the delivery system 602 having features consistent with the current subject matter. FIG. 6B is an illustration 604 of the delivery system 602 as illustrated in FIG. 6A with the pulse generator 102 mounted in it. Delivery system 602 can be configured to facilitate implantation of the pulse generator 102 into the thoracic region of a patient.

Delivery system 602 includes a proximal end 606 and a distal end 608. The distal end 608 of delivery system 602 contains a receptacle 610 in which the housing of the pulse generator 102 is loaded. Where the pulse generator 102 contains a connection lead, the delivery system 602 can be configured to accommodate the connection lead so that the connection lead will not be damaged during the implantation of the pulse generator 102.

When pulse generator 102 is fully loaded into delivery system 602, pulse generator 102 is substantially embedded into the receptacle 610. In some variations, a portion of the pulse generator 102's distal end can be exposed, protruding from the end of receptacle 610. The tapered shape of the distal end 106 of pulse generator 102 can be used in conjunction with the delivery system 602 to assist with separating tissue planes as delivery system 602 is used to advance pulse generator 102 to its desired location within the patient.

In some variations, the entirety of pulse generator 102 can be contained within receptacle 610 of the delivery system 602. The pulse generator 102 in such a configuration will not be exposed during the initial advancement of delivery system 602 into the patient. The distal end 608 of delivery system 602 may be designed to itself separate tissue planes within the patient as delivery system 602 is advanced to the desired location within the patient.

The pulse generator delivery system 602 may be made from a polymer, a metal, a composite material or other suitable material. Pulse generator delivery system 602 can include multiple components. Each component of the pulse generator delivery system 602 can be formed from a material suitable to the function of the component. The pulse generator delivery system 602 can be made from a material capable of being sterilized for repeated use with different patients.

Pulse generator delivery system 602 may include a handle 612. Handle 612 can facilitate advancement of delivery system 602 and pulse generator 102 into a patient's body. Handle 612 can be disposed on either side of the main body 614 of the delivery system 602, as illustrated in FIGS. 6A and 6B. In some variations, handle 612 can be disposed on just one side of the main body 614 of the delivery system 602. The handle 612 can be configured to be disposed parallel to plane of insertion and advancement 616 of pulse generator delivery system 602 within the body. In some variations, handle 612 can be located orthogonally to the plane of insertion and advancement 616 of the delivery system 602. Handle 612 can be configured to facilitate the exertion of pressure, by a physician, onto the pulse generator delivery system 602, to facilitate the advancement and positioning of the delivery system 602 at the desired location within the patient.

Pulse generator delivery system 602 can include a pulse generator release device 618. The release device 618 can be configured to facilitate disengagement of the pulse generator 102 from the delivery system 602. In some variations, release device 618 can include a plunger 620. Plunger 620 can include a distal end configured to engage with the proximal end 606 of the pulse generator delivery system 602. The plunger 620 can engage with the proximal end 606 of the pulse generator delivery system 602 when the pulse generator 102 is loaded into the receptacle 610 of the delivery system 602. The proximal end 622 of the plunger 620 can extend from the proximal end 606 of the delivery system 602.

Plunger 620 can include a force applicator 624. Force applicator 624 can be positioned at the proximal end 622 of plunger 620. Force applicator 624 can be configured to facilitate application of a force to the plunger 620 to advance the plunger 620. Advancing plunger 620 can force pulse generator 102 from the delivery system 602. In some variations, the force applicator 624 can be a ring member. The ring member can facilitate insertion, by the physician, of a finger. Pressure can be applied to the plunger 620 through the ring member, forcing the pulse generator 102 out of the receptacle 610 of the delivery system 602 into the patient at its desired location. In some variations, the proximal end 622 of the plunger 620 can include a flat area, for example, similar to the flat area of a syringe, that allows the physician to apply pressure to the plunger 620. In some variations, the plunger 620 can be activated by a mechanical means such as a ratcheting mechanism.

The distal end 608 of the pulse generator delivery device 602 can include one or more sensors. The sensor(s) can be configured to facilitate detection of a state of patient tissues adjacent distal end 608 of the pulse generator delivery device 602. Various patient tissues can emit, conduct and/or reflect signals. The emitted, conducted and/or reflected signals can provide an indication of the type of tissue encountered by the distal end 608 of the pulse generator delivery device 602. Such sensor(s) can be configured, for example, to detect the electrical impedance of the tissue adjacent the distal end 608 of the pulse generator delivery device 602. Different tissues can have different levels of electrical impedance. Monitoring the electrical impedance can facilitate a determination of the location, or tissue plane, of the distal end 608 of the delivery device 602.

In addition to delivery of the pulse generator, delivery of at least one lead for sensing and/or transmitting therapeutic electrical pulses from the pulse generator is typically required. Proper positioning of the distal end of such lead(s) relative to the heart is very important. Delivery systems are provided that can facilitate the insertion of one or more leads to the correct location(s) in the patient. The delivery systems can facilitate finding the location of the initial insertion point for the lead. The initial insertion point optionally being an intercostal space associated with a patient's cardiac notch of the left lung. The intercostal spaces associated with the cardiac notch commonly include the left-hand-side fourth, fifth and sixth intercostal spaces. Other intercostal spaces on either side of the sternum may be used, especially when the patient is experiencing conditions that prevent use of the fourth, fifth and sixth intercostal spaces, or due to anatomical variations.

When making the initial insertion through the epidermis and the intercostal muscles of the patient, it is important to avoid damaging important blood-filled structures of the patient. Various techniques can be employed to avoid damaging important blood-filled structures. For example, sensors can be used to determine the location of the blood-filled structures. Such sensors may include accelerometers configured to monitor pressure waves caused by blood flowing through the blood-filed structures. Sensors configured to emit and detect light-waves may be used to facilitate locating tissues that absorb certain wavelengths of light and thereby locate different types of tissue. Temperature sensors may be configured to detect differences in temperature between blood-filled structures and surrounding tissue. Lasers and detectors may be employed to scan laser light across the surface of a patient to determine the location of subcutaneous blood-filled structures.

Conventional medical devices may be employed to locate the desired initial insertion point into the patient. For example, x-ray machines, MRI machines, CT scanning machines, fluoroscopes, ultrasound machines and the like, may be used to facilitate determination of the initial insertion point for the leads as well as facilitate in advancing the lead into the patient.

Advancing a lead into a patient can also present the risk of damaging physiological structures of the patient. Sensors may be employed to monitor the characteristics of tissues within the vicinity of the distal end of an advancing lead. Readings from sensors associated with the characteristics of tissues can be compared against known characteristics to determine the type of tissue in the vicinity of the distal end of the advancing lead.

Sensors, such as pH sensors, thermocouples, accelerometers, electrical impedance monitors, and the like, may be used to detect the depth of the distal end of the electrode in the patient. Physiological characteristics of the body change the further a lead ventures into it. Measurements performed by sensors at, or near, the distal end of the advancing lead may facilitate the determination of the type of tissue in the vicinity of the distal end of the lead, as well as its depth into the patient.

Various medical imaging procedures, may be used on a patient to determine the location of the desired positions in the heart for the distal end of the lead(s). This information can be used, in conjunction with sensor readings, of the kind described herein, to determine when the distal end of the lead has advanced to a desired location within the patient.

Components may be used to first create a channel to the desired location for the distal end of the lead. Components can include sheathes, needles, cannulas, balloon catheters and the like. A component may be advanced into the patient with the assistance of sensor measurements to determine the location of the distal end of the component. Once the component has reached the desired location, the component may be replaced with the lead or the lead may be inserted within the component. An example of a component can include an expandable sheath. Once the sheath has been advanced to the desired location, a cannula extending the length of the sheath may be expanded, allowing a lead to be pass through the cannula. The sheath may then be removed from around the lead, leaving the lead in situ with the distal end of the lead at the desired location.

Determination of the final placement of the distal end of a lead is important for the delivery of effective therapeutic electrical pulses for pacing the heart. The present disclosure describes multiple technologies to assist in placement of a lead in the desired location. For example, the use of sensors on the pulse generator, on the distal end of leads, or on delivery components. In addition, when a lead or component is advanced into a patient, balloons may be employed to avoid damaging physiological structures of the patient. Inflatable balloons may be disposed on the distal end of the lead or component, on the sides of a lead body of the lead, or may be circumferentially disposed about the lead body. The balloons may be inflated to facilitate the displacement of tissue from the lead to avoid causing damage to the tissue by the advancing lead. A lead delivery assembly may also be used to facilitate delivery of the lead to the desired location. In some variations, the lead delivery assembly may be configured to automatically deliver the distal end of the lead to the desired location in the patient. Such a lead delivery system is disclosed in co-owned U.S. patent application Ser. No. 14/846,578, filed Sep. 4, 2015, the disclosure of which is incorporated herein by reference.

FIG. 7 is an illustration 700 of an exemplary process flow illustrating a method of delivering a lead having features consistent with the present disclosure. At 702, the location of blood-filled structures, in the vicinity of an intercostal space, can be determined. The intercostal space can be an intercostal space associated with the cardiac notch of the patient. Determining the location of the blood-filed structures may be facilitated by one or more sensors configured to detect the location of blood-filled structures.

At 704, a region can be chosen for advancing of a lead through intercostal muscles associated with the cardiac notch. The region chosen may be based on the determined location of blood-filled structures of the patient in that region. It is important that damage to blood-filled structures, such as arteries, veins, and the like, is avoided when advancing a lead into a patient.

At 706, a lead can be advanced through the intercostal muscles associated with the cardiac notch of the patient. Care should be taken to avoid damaging important physiological structures. Sensors, of the kind described herein, may be used to help avoid damage to important physiological structures.

At 708, advancement of the lead through the intercostal muscles can be ceased. Advancement may be ceased in response to an indication that the distal end of the lead has advanced to the desired location. Indication that the distal end of the lead is at the desired location may be provided through measurements obtained by one or more sensors of the kind described herein.

Figure 8A:
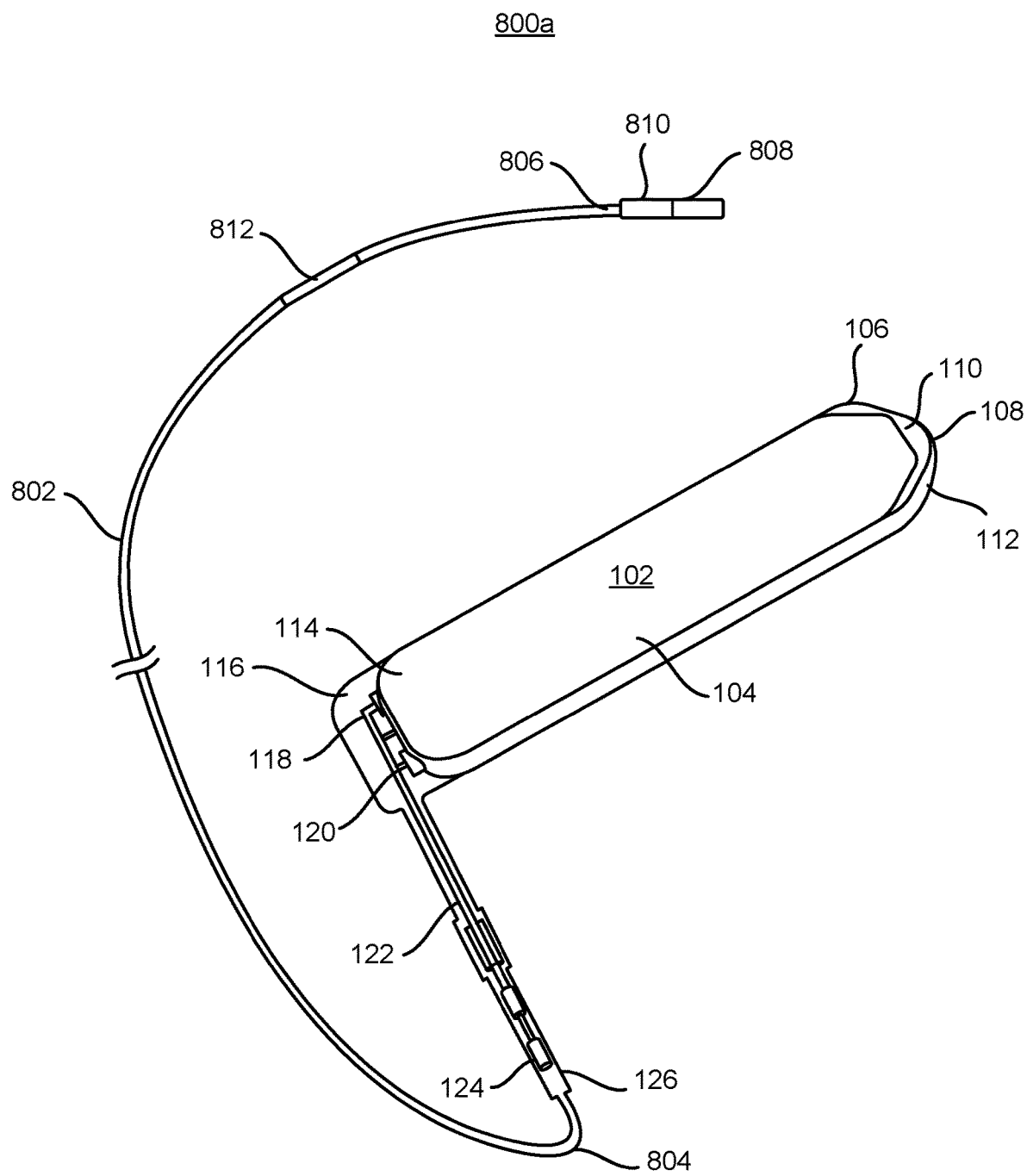
FIG. 8A is an illustration of an exemplary lead having features consistent with the current subject matter.

The lead advanced through the intercostal muscles associated with the cardiac notch of the patient can be configured to transmit therapeutic electrical pulses to pace the patient's heart. FIG. 8A is an illustration 800a of an exemplary lead 802 having features consistent with the present disclosure. For the lead to deliver therapeutic electrical pulses to the heart for pacing the heart, a proximal end 804 of lead 802 is configured to couple with the pulse generator 102. The proximal end 804 of lead 802 may be configured to couple with a connection port 124. The connection port can be configured to couple the proximal end 804 of lead 802 to one or more conductors, such as conductors 118 and 120. When the proximal end 804 of lead 802 couples with connection port 124, a sealed housing may be formed between them. In some variations, the materials of connection port 124 and the proximal end 804 of lead 802 may be fused together. In some variations, the proximal end 804 of lead 802 may be configured to be pushed into the sealed housing 126, or vice versa. Optionally, the external diameter of the inserted member may be slightly greater than the internal diameter of the receiving member causing a snug, sealed fit between the two members. Optionally, a mechanism, such as a set-screw or mechanical lock, may be implemented upon the connection port 124 or proximal lead end 804 in order to prevent unintentional disconnection of the lead 802 from pulse generator 102.

Also shown in FIG. 8A is the distal end 806 of lead 802. The distal end 806 of lead 802 may comprise an electrode 808. In some variations, lead 802 may include a plurality of electrodes. In such variations, lead 802 may include a multiple-pole lead. Individual poles of the multiple-pole lead can feed into separate electrodes. Electrode 808 at the distal end 806 of lead 802 may be configured to deliver electrical pulses to pace the heart when located in the desired position for pacing the heart.

The distal end 806 of lead 802 can include one or more sensors 810. Sensor(s) 810 can be configured to monitor physiological characteristics of the patient while the distal end 806 of lead 802 is being advanced into the patient. Sensors can be disposed along the length of lead 802. For example, sensor 812 is disposed some distance from the distal end 806. Such sensors incorporated onto the lead can detect subtle physiological, chemical and electrical differences that distinguish the lead's placement within the desired location, as opposed to other locations in the patient's thoracic cavity.

In some variations, the proximal end 804 of lead 802 may be coupled with pulse generator 102 prior to the distal end 806 of lead 802 being advanced through the intercostal space of the patient. In some variations, the proximal end 804 of the lead 802 may be coupled with pulse generator 102 after the distal end 806 of lead 802 has been advanced to the desired location.

To assist in the placement of the lead, various medical instruments may be used. The medical instruments may be used alone, or in combination with sensors disposed on the lead that is being placed. Medical instruments may be used to help the physician to access the desired location for the placement of a lead and/or confirm that the distal end of the lead has reached the desired location. For example, instruments, such as an endoscope or laparoscopic camera, with its long, thin, flexible (or rigid) tube, light and video camera can assist the physician in confirming that the distal end 806 of lead 802 has reached the desired location within the thoracic cavity. Other tools known to one skilled in the art such as a guidewire, guide catheter, or sheath may be used in conjunction with medical instruments, such as the laparoscopic camera, and may be advanced alongside and to the location identified by the medical instruments. Medical instruments such as a guidewire can be advanced directly to the desired location for the distal end of the lead with the assistance of acoustic sound, ultrasound, real-time spectroscopic analysis of tissue, real-time density analysis of tissue or by delivery of contrast media that may be observed by real-time imaging equipment.

In some variations, the patient may have medical devices previously implanted that may include sensors configured to monitor physiological characteristics of the patient. The physiological characteristics of the patient may change based on the advancement of the lead through the intercostal space of the patient. The previously implanted medical device may have sensors configured to detect movement of the advancing lead. The previously implanted medical device can be configured to communicate this information back to the physician to verify the location of the advancing lead.

Sensors disposed on the lead, such as sensors 810 disposed on distal end 806 of the lead may be used to facilitate the delivery of the lead to the desired location. Sensor(s) 810 can be configured to facilitate determination of a depth of the distal end 806 of lead 802. As described above, the depth of the desired location within the patient can be determined using one or more medical instruments. This can be determined during implantation of the lead 802 or prior to the procedure taking place.

Although sensor(s) 810 is illustrated as a single element in FIG. 8A, sensor(s) 810 can include multiple separate sensors. The sensors 810 can be configured to facilitate placement of the distal end 806 of the lead 802 at a desired location and verification thereof.

Sensor(s) 810 can be configured to transmit sensor information during advancement to the desired location. Sensor(s) 810 may transmit signals associated with the monitored physiological characteristics of the tissue within the vicinity of the distal end 806 of the lead 802. In some variations, the signals from sensor(s) 810 may be transmitted to a computing device(s) configured to facilitate placement of the lead 802 in the desired location. In such variations, the computing device(s) can be configured to assess the sensor information individually, or in the aggregate, to determine the location of the distal end 806 of lead 802. The computing device(s) can be configured to present alerts and/or instructions associated with the position of the distal end 806 of lead 802.

In some variations, lead 802 can be first coupled with connection port 124 of pulse generator 102. Signals generated by sensor(s) 810 can be transmitted to a computing device(s) using transceiver 316 in pulse generator 102, as illustrated in FIG. 3.

An accelerometer may be used to facilitate delivery of the distal end 806 of lead 802 to the desired location. An accelerometer may be disposed at the distal end 806 of lead 802. The accelerometer may be configured to monitor the movement of the distal end 806 of lead 802. The accelerometer may transmit this information to a computing device or the physician. The computing device, or the physician, can determine the location of the distal end 806 of the lead 802 based on the continuous movement information received from the accelerometer as the lead 802 is advanced into the patient. The computing device or the physician may know the initial entry position for lead 802. The movement information can indicate a continuous path taken by the lead 802 as it advanced into the body of the patient, thereby providing an indication of the location of the distal end 806 of lead 802. Pressure waves from the beating heart may differ as absorption changes within deepening tissue planes. These pressure wave differences may be used to assess the depth of the distal end of the electrode.

The accelerometer can also be configured to monitor acoustic pressure waves generated by various anatomical structures of the body. For example, the accelerometer can be configured to detect acoustic pressure waves generated by the heart or by other anatomical structures of the body. The closer the accelerometer gets to the heart, the greater the acoustic pressure waves generated by the heart will become. By comparing the detected acoustical pressure waves with known models, a location of the distal end 806 of lead 802 can be determined.

Pressure waves or vibrations can be artificially generated to cause the pressure waves or vibrations to traverse through the patient. The pressure waves or vibrations can be generated in a controlled manner. The pressure waves or vibrations may be distorted as they traverse through the patient. The level of type of distortion that is likely to be experienced by the pressure waves or vibrations may be known. The pressure waves or vibrations detected by the accelerometer can be compared to the known models to facilitate determination or verification of the location of the distal end 806 of lead 802.

Different tissues within a body exhibit different physiological characteristics. The same tissues situated at different locations within the body can also exhibit different physiological characteristics. Sensors, disposed on the distal end 806, of lead 802 can be used to monitor the change in the physiological characteristics as the distal end 806 is advanced into the body of the patient. For example, the tissues of a patient through which a lead is advanced can demonstrate differing resistances, physiological properties, electrical impedance, temperature, pH levels, pressures, and the like. These different physiological characteristics, and the change in physiological characteristics, experienced as a sensor traverses through a body can be known or identified. For example, even if the actual degree is not known ahead of time, the change in sensor input when the sensor traverses from one tissue media to another may be identifiable in real-time. Consequently, sensors configured to detect physiological characteristics of a patient can be employed to facilitate determining and verifying the location of the distal end 806 of lead 802.

Different tissues can exhibit different insulative properties. The insulative properties of tissues, or the change in insulative properties of tissues, between the desired entry-point for the lead and the desired destination for the lead can be known. Sensor 810 can include an electrical impedance detector. An electrical impedance detector can be configured to monitor the electrical impedance of the tissue in the vicinity of the distal end 806 of lead 802. The electrical impedance of the tissue monitored by the electrical impedance detector can be compared with the known insulative properties of the tissues between the entry point and the destination, to determine the location of the distal end of lead 802 or a transition from one tissue plane to another may be recognized by a measurable change in the measured impedance.

Varying levels of electrical activity can be experienced at different locations with the body. Electrical signals emitted from the heart, or other muscles can send electrical energy through the body. This electrical energy will dissipate the further it gets from its source. Various tissues will distort the electrical energy in different ways. Sensors configured to detect the electrical energy generated by the heart and/or other anatomical structures can monitor the electrical energy as the lead is advanced. By comparing the monitored electrical energy with known models, a determination or verification of the location of the distal end 806 of lead 802 can be made. The sensors may be configured to identify sudden changes in the electrical activity caused by advancement of the sensor into different tissue planes.

Tissues throughout the body have varying pH levels. The pH levels of tissues can change with depth into the body. Sensor(s) 810 can include a pH meter configured to detect the pH levels of the tissue in the vicinity of the sensor(s) 810 as the sensor(s) advance through the patient. The detected pH levels, or detected changes in pH levels, can be compared with known models to facilitate determination or verification of the location of the distal end 806 of lead 802. The pH meter may be configured to identify sudden changes in the pH level caused by advancement of the meter into different tissue planes.

Different tissues can affect vibration-waves or sound-waves in different ways. Sensor(s) 810 can include acoustic sensors. The acoustic sensors can be configured to detect vibration waves or sound waves travelling through tissues surrounding sensor(s) 810. The vibration waves can be emitted by vibration-emitting devices embedded the lead 802. The vibration waves can be emitted by vibration-emitting devices located on a hospital gurney, positioned on the patient, or otherwise remote from lead 802. Sensor(s) 810 can be configured to transmit detected vibration-wave information to a computing device configured to determine the location of the distal end 806 of lead 802 based on the detected vibration-wave information.

Different tissues can have different known effects on the emitted electromagnetic waves. Sensors can be used to detect the effect that the tissue in the vicinity of the sensors have on the electromagnet waves. By comparing the effect that the tissue has on the electromagnetic waves with known electromagnetic effects, the identity of the tissue can be obtained and the location of the lead can be determined or verified. For example, sensor(s) 810 can include electromagnetic wave sensors. Electromagnetic wave sensors can include an electromagnetic wave emitter and an electromagnetic wave detector. The electromagnetic waves will be absorbed, reflected, deflected, and/or otherwise affected by tissue surrounding sensor(s) 810. Sensor(s) 810 can be configured to detect the change in the reflected electromagnetic waves compared to the emitted electromagnetic waves. By comparing the effect the tissue in the vicinity of the sensor(s) 810 has on the electromagnetic waves with known models, a determination verification of the location of lead 802 can be made. The sensors may be configured to identify sudden changes in the electromagnetic activity caused by advancement of the sensor into different tissue planes.

Figure 9A:
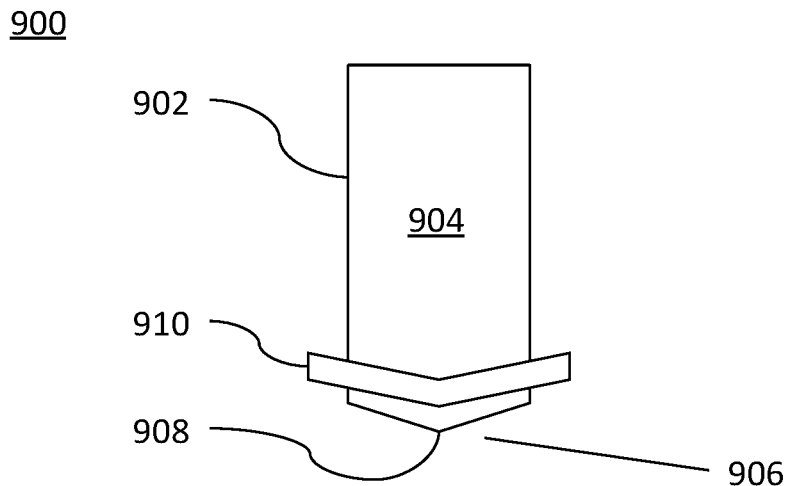
FIG. 9A is an illustration of the distal end of an exemplary delivery system having features consistent with the current subject matter.

FIG. 9A is an illustration 900 of the distal end of an exemplary delivery system 902 having features consistent with the presently described subject matter. While FIG. 9A is described with reference to a delivery system, one of ordinary skill in the art can appreciate and understand that the technology described herein could be applied directly to the end of a lead, such as lead 802. The present disclosure is intended to apply to a delivery system, such as delivery system 902, as well as a lead, such as lead 802.

Delivery system 902 can facilitate placement of the distal end of a lead, such as lead 802 illustrated in FIG. 8, to a desired location by use of electromagnetic waves, such as light waves. Delivery system 902 may comprise a delivery catheter body 904. Delivery catheter body 904 may be configured to facilitate advancement of delivery catheter body 904 into the patient to a desired location. The distal tip 906 of delivery catheter body 904 may comprise a light source 908. Light source 908 can be configured to emit photons having a visible wavelength, infrared wavelength, ultraviolet wavelength, and the like. Delivery catheter body 904 may comprise a light detector 910. Light detector 910 may be configured to detect light waves, emitted by the light source 908, reflected by tissues surrounding distal tip 906 of delivery catheter body 904.

Figure 9B:
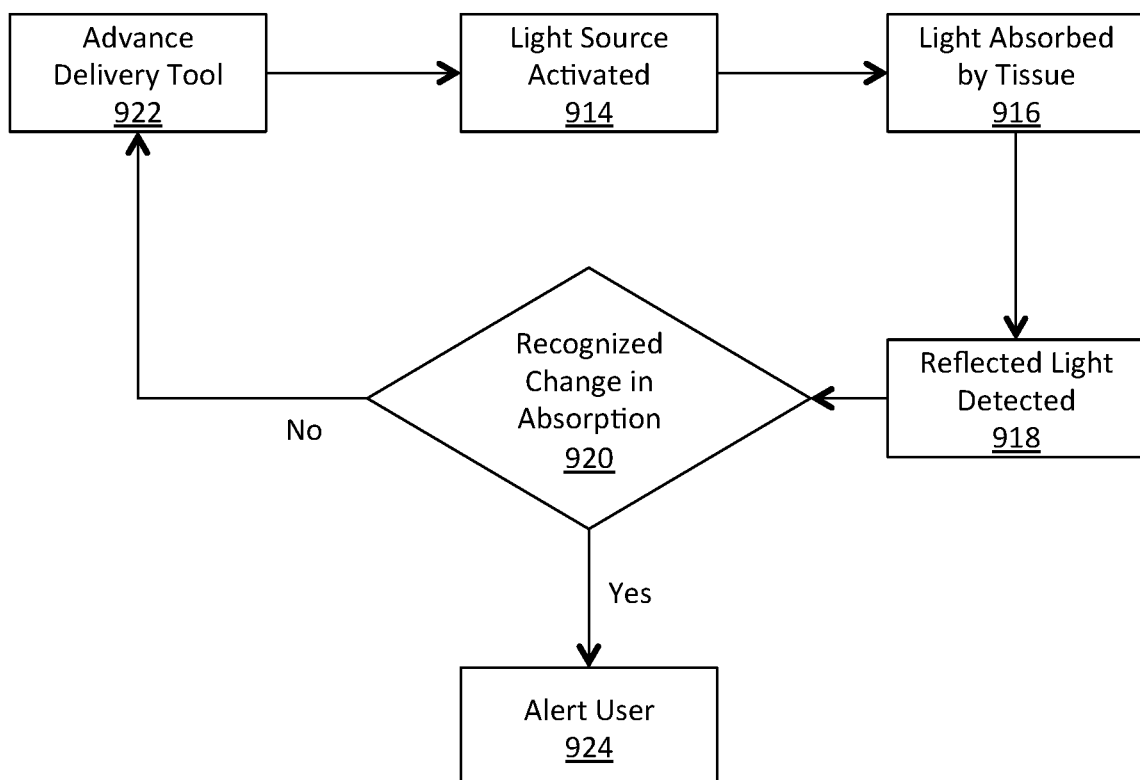
FIG. 9B is an illustration of an exemplary process for using the delivery system illustrated in FIG. 9A.

FIG. 9B is an illustration 912 of an exemplary process for using the delivery system illustrated in FIG. 9A. Light detector 910 can be configured to detect light waves reflected by the tissue adjacent the distal end 906 of delivery system 902. Information associated with the detected light waves may be transmitted to a computing device. The computing device can be configured to interpret the information transmitted from light detector 910 and determine a difference between the light emitted and the light detected.

At 914, light source 908 can be activated. Light source 908 may emit light-waves into the tissue in the general direction of the intended advancement of delivery system 902. At 916, the tissue can absorb a portion of the emitted light waves. At 918, light detector 910 can detect the reflected light waves, reflected by tissues surrounding light source 908. At 920, a determination of a change in the absorption of the light waves by tissues surrounding the distal tip 906 of delivery system 902 can be made.

At 922, in response to an indication that the absorption of light waves has not changed, delivery system 902 can be configured to advance a delivery system, such as delivery system 902, into the patient. In some variations, a physician can advance delivery system 902 into the patient. In other variations, the delivery system 902 can be advanced into the patient automatically.

At 924, in response to an indication that the absorption of light waves has changed, an alert can be provided to the physician. In some variations, the alert can be provided to the physician through a computing device configured to facilitate positioning of delivery system 902 into the patient.

In some variations, a computing device may be configured to facilitate positioning of delivery system 902 into the patient. The computing device can be configured to alert the physician to the type of tissue in the vicinity of distal tip 906 of delivery system 902. In some variations, the computing device can be configured to alert the physician when the distal tip 906 reaches a tissue having characteristics consistent with the desired location of the distal tip 906 of delivery system 902. For example, when the characteristics of the tissue in the vicinity of the distal tip 906 match those within the intercostal tissues, or a particular location within the medistiunum, an alert may be provided.

Blood vessels, both venous and arterial, absorb red, near infrared and infrared (IR) light waves to a greater degree than surrounding tissues. When illuminating the surface of the body with red, near infrared and infrared (IR) light waves, blood rich tissues, for example veins, will absorb more of this light than other tissues, and other tissues will reflect more of this light than the blood rich tissues. Analysis of the pattern of reflections can enable the blood rich tissues to be located. A positive or negative image can be projected on the skin of the patient at the location of the vein. In some variations, the vein can be represented by a bright area and the absence of a vein can be represented as a dark area, or vice versa.

Delivery system 902 can include a subcutaneous visualization enhancer. The subcutaneous visualization enhancer may be configured to enhance visualization of veins, arteries, and other subcutaneous structures of the body. The subcutaneous visualization enhancer can include moving laser light sources to detect the presence of blood-filled structures, such as venous or arterial structures below the surface of the skin. The subcutaneous visualization enhancer can include systems configured to project an image onto the surface of the skin that can show an operator the pattern of the detected subcutaneous blood-filled structures. Laser light from laser light sources can be scanned over the surface of the body using mirrors. A light detector can be configured to measure the reflections of the laser light and use the pattern of reflections to identify the targeted blood rich structures.

Such subcutaneous visualization enhancers can be used to facilitate determination of the location for the initial approach for inserting a lead, such as lead 802, through the intercostal space associated with the cardiac notch of the patient. In some variations, the visualization enhancers can be disposed remote from the delivery system and/or can be configured to enhance visualization enhancers disposed on the delivery system.

With the provision of a visualization of the detected subcutaneous structures, the physician can assess the position of subcutaneous structures such as the internal thoracic artery, or other structures, of the body while concurrently inserting components of the delivery system into the body, while avoiding those subcutaneous structures.

In some variations, during advancement of lead 802 through the intercostal space associated with the cardiac notch, sensor(s) 810 can be configured to transmit obtained readings to a computing device for interpretation. In some variations, the computing device is pulse generator 102. In some variations, pulse generator 102 is used to transmit the readings to an external computing device for interpretation. In any event, the sensor information from the various sensors can be used individually, or accumulatively, to determine the location of the distal end of lead 802.

Figure 10:
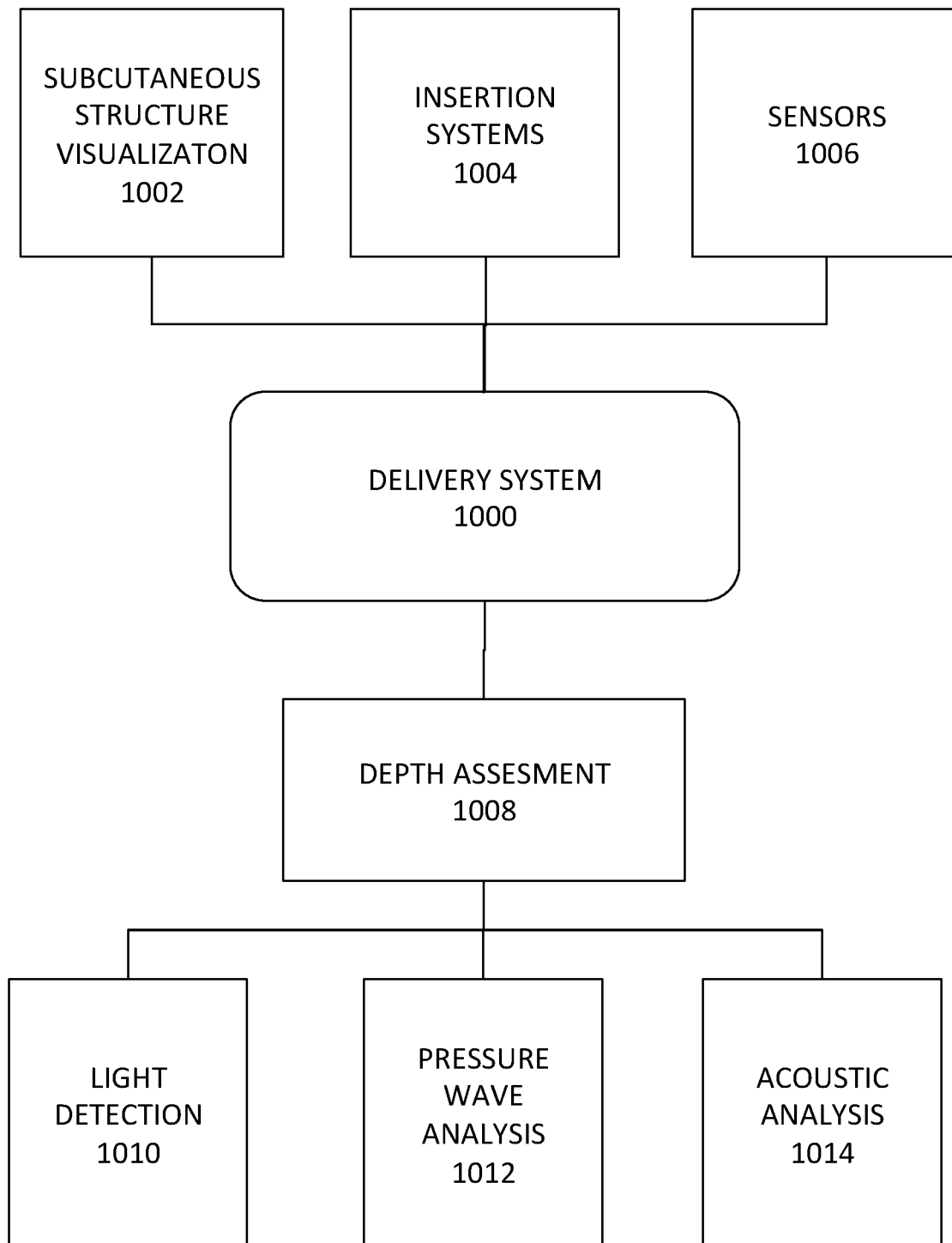
FIG. 10 is a schematic illustration of an exemplary delivery control system having features consistent with the current subject matter.

FIG. 10 is a schematic illustration of a delivery control system 1000 having features consistent with the current subject matter. The delivery control system 1000 can be configured to automatically deliver a lead to the desired position within the patient. For example, the delivery control system 1000 can be configured to automatically deliver a distal tip of a lead through the intercostal space associated with the cardiac notch.

Delivery control system 1000 can be configured to receive a plurality of inputs. The inputs can come from one or more sensors disposed in, or on, the patient. For example, delivery control system 1000 can be configured to receive subcutaneous structure visualization information 1002, information associated with delivery insertion systems 1004, information associated with sensors 1006, and the like.

Delivery control system 1000 can be configured to use remote sensors 1006 to facilitate determination of the insertion site for the lead. Sensors 1006 can be disposed in various instruments configured to be inserted into the patient. Sensors 1006 can also be disposed in various instruments configured to remain external to the patient.

Delivery control system 1000 can be configured to perform depth assessments 1008. The depth assessments 1008 can be configured to determine the depth of the distal end of an inserted instrument, such as a lead 802 illustrated in FIG. 8A. Depth assessments 1008 can be configured to determine the depth of the distal end of the inserted instrument through light detection systems 1010, pressure wave analysis 1012, acoustic analysis, and the like.

Depth assessments 1008 can be configured to determine the depth of the delivery system, or lead, though pressure wave analysis systems 1012. Pressure waves can be detected by accelerometers as herein described.

Depth assessments 1008 can be configured to determine the depth of the delivery system though acoustic analysis systems 1014. Acoustic analysis system 1014 can be configured to operate in a similar manner to a stethoscope. The acoustic analysis system 1014 can be configured to detect the first heart sound (S1), the second heart sound (S2), or other heart sounds. Based on the measurements obtained by the acoustic analysis system 1014, a depth and/or location of the distal end of a delivery system and/or inserted medical component can be determined. The acoustic analysis system 1014 can be configured to measure the duration, pitch, shape, and tonal quality of the heart sounds. By comparing the duration, pitch, shape, and tonal quality of the heart sounds with known models, a determination or verification of the location of the lead can be made. Sudden changes in the degree of heart sounds may be used to indicate advancement into a new tissue plane.

In some variations, the lead can include markers or sensors that facilitate the correct placement of the lead. Certain markers such as a visual scale, radiopaque, magnetic, ultrasound markers, and the like, can be position at defined areas along the length of the lead so that the markers can be readily observed by an implanting physician, or automated system, on complementary imaging instruments such as fluoroscopy, x-ray, ultrasound, or other imaging instruments known in the art. Through the use of these markers, the physician, or automated implantation device, can guide the lead to the desired location within the intercostal muscle, pleural space, mediastinum, or other desired position, as applicable.

Figure 11A:
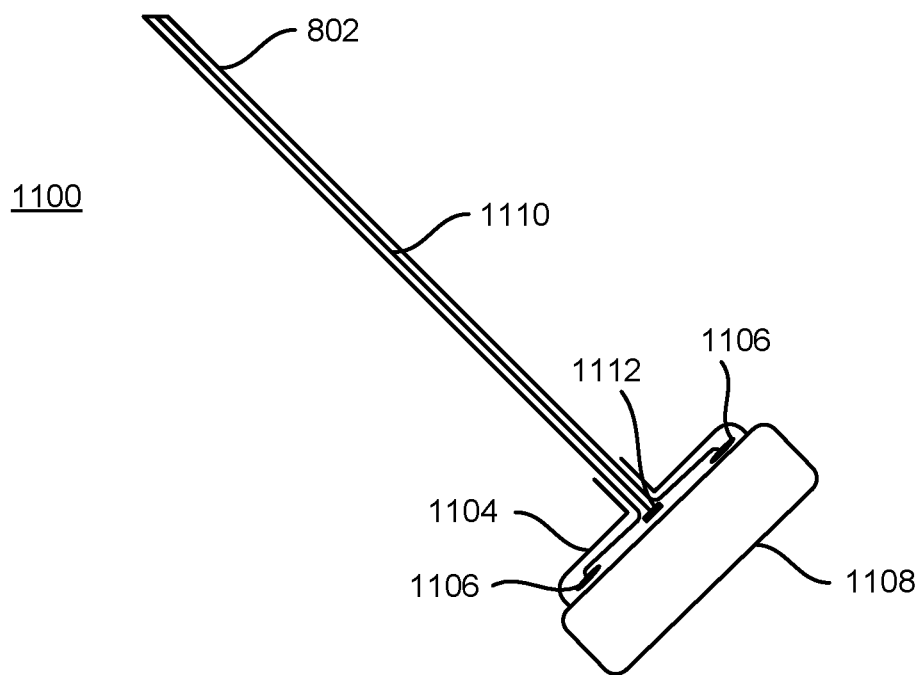
FIGS. 11A and 11B are illustrations of an exemplary lead having features consistent with the current subject matter.
Figure 11B:
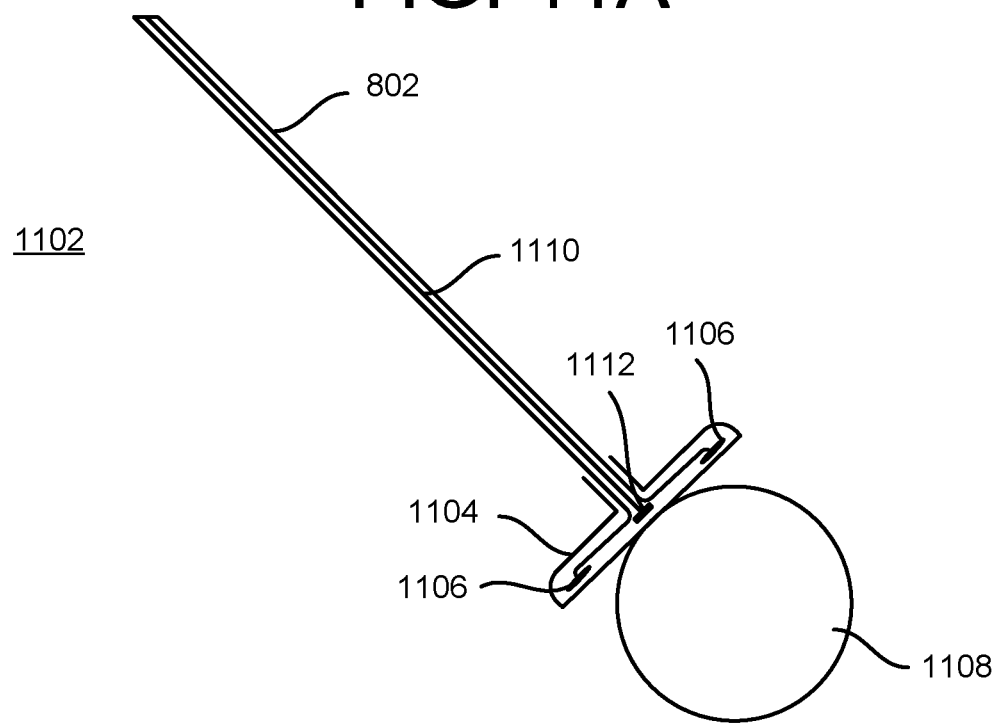

Avoiding damage to tissues in the vicinity of the path-of-travel for the lead is important. Moving various tissues from the path of the lead without damaging them is also important. FIGS. 11A and 11B are illustrations 1100 and 1102 of an exemplary lead 802 having features consistent with the present disclosure for moving and avoiding damage to tissues during lead delivery. Lead 802 can comprise a distal tip 1104. Distal tip 1104 can include at least one electrode and/or sensor 1106.

Having leads directly touch the tissue of a patient can be undesirable and can damage the tissue. Consequently, the distal tip 1106 of lead 802 can include an inflatable balloon 1108. Balloon 1108 can be inflated when the distal tip 1106 of lead 802 encounters an anatomical structure obstructing its path, or prior to moving near sensitive anatomy during lead delivery. The balloon may be configured to divert the obstacle and/or the lead to facilitate circumventing the anatomical structure or may indicate that the lead has reached its intended destination.

To inflate the balloon, lead 802 can include a gas channel 1110. At the end of gas channel 1110 there can be a valve 1112. Valve 1112 can be controlled through physical manipulation of a valve actuator, through electrical stimulation, through pressure changes in gas channel 1110 and/or controlled in other ways. In some variations, the valve 1112 may be configured at the proximal end of the lead 802.

When positioning lead 802 into a patient, lead 802 may cause damage to, or perforations of, the soft tissues of the patient. When lead 802 is being installed into a patient, distal tip 1104 of lead 802 can encounter soft tissue of the patient that should be avoided. In response to encountering the soft tissue of the patient, gas can be introduced into gas channel 1110, valve 1112 can be opened and balloon 1108 can be inflated, as shown in FIG. 11B. Inflating balloon 1108 can cause the balloon to stretch and push into the soft tissue of the patient, moving the soft tissue out of the way and/or guiding distal tip 1104 of lead 802 around the soft tissue. When distal tip 1104 of lead 802 has passed by the soft tissue obstruction, valve 1112 can be closed and the balloon deflated.

Figure 12:
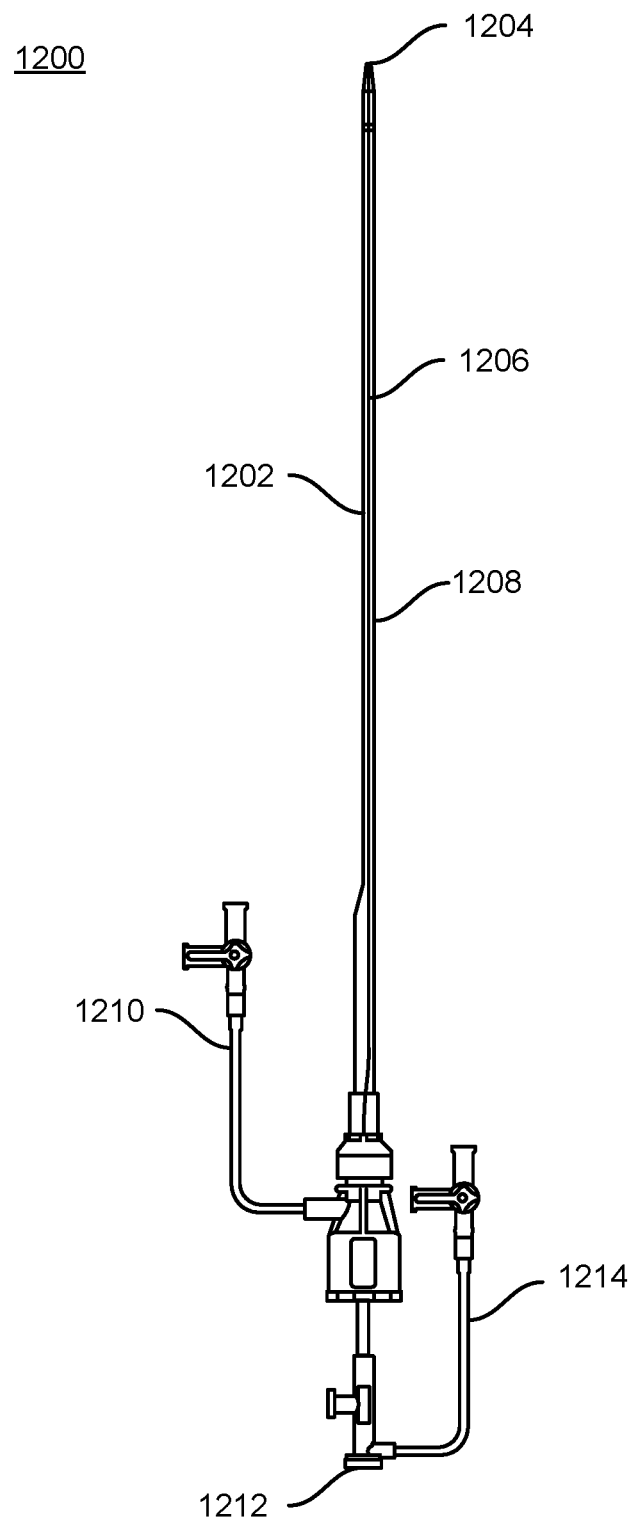
FIG. 12 is an illustration of an exemplary sheath for delivering a lead, the sheath having features consistent with the current subject matter.

In some variations, a delivery component or system is used to facilitate delivery of a lead, such as lead 802, to the desired location. FIG. 12 is an illustration 1200 of an exemplary delivery system for a lead having features consistent with the present disclosure. An example of the delivery system is an expandable sheath 1202. Expandable sheath 1202 can be inserted into the patient at the desired insertion point, identified using one or more of the technologies described herein. Expandable sheath 1202 can include a tip 1204. In some variations, tip 1204 may be radiopaque. A radiopaque tip 1204 may be configured to facilitate feeding of the expandable sheath 1202 to a desired location using one or more radiography techniques known in the art and described herein. Such radiography techniques can include fluoroscopy, CT scan, and the like.

Tip 1204 can include one or more sensors for facilitating the placement of the lead. The sensors included in tip 1204 of the expandable sheath 1202 can be the same or similar to the sensors described herein for monitoring physiological characteristics of the body and other characteristics for facilitating positioning of a lead in a body.

Expandable sheath 1202 can include a channel 1206 running through a hollow cylinder 1208 of expandable sheath 1202. When tip 1204 of expandable sheath 1202 is at the desired location, gas or liquid can be introduced into hollow cylinder 1208. The gas or liquid can be introduced into hollow cylinder 1208 through a first port 1210. Hollow cylinder 1208 can expand, under the pressure of the gas or liquid, causing channel 1206 running through hollow cylinder 1208 to increase in size. A lead, such as lead 802 illustrated in FIG. 8A, can be inserted into channel 1206 through a central port 1212. Hollow cylinder 1208 can be expanded until channel 1206 is larger than the lead. In some variations, channel 1206 can be expanded to accommodate leads of several French sizes. Once the lead is in the desired place, expandable sheath 1202 can be removed, by allowing the lead to pass through channel 1206. In some variations, liquid or gas can be introduced into or removed from channel 1006 through a second port 1214.

Using expandable sheath 1202 can provide an insertion diameter smaller than the useable diameter. This can facilitate a reduction in the risk of damage to tissues and vessels within the patient when placing the lead.

When electricity is brought within the vicinity of muscle tissue, the muscle will contract. Consequently, having a lead for carrying electrical pulses traversing through intercostal muscle tissue may cause the intercostal muscle tissue to contract. Electrical insulation can be provided in the form of a receptacle disposed in the intercostal muscle, where the receptacle is configured to electrically insulate the intercostal muscle from the lead.

Figure 13:
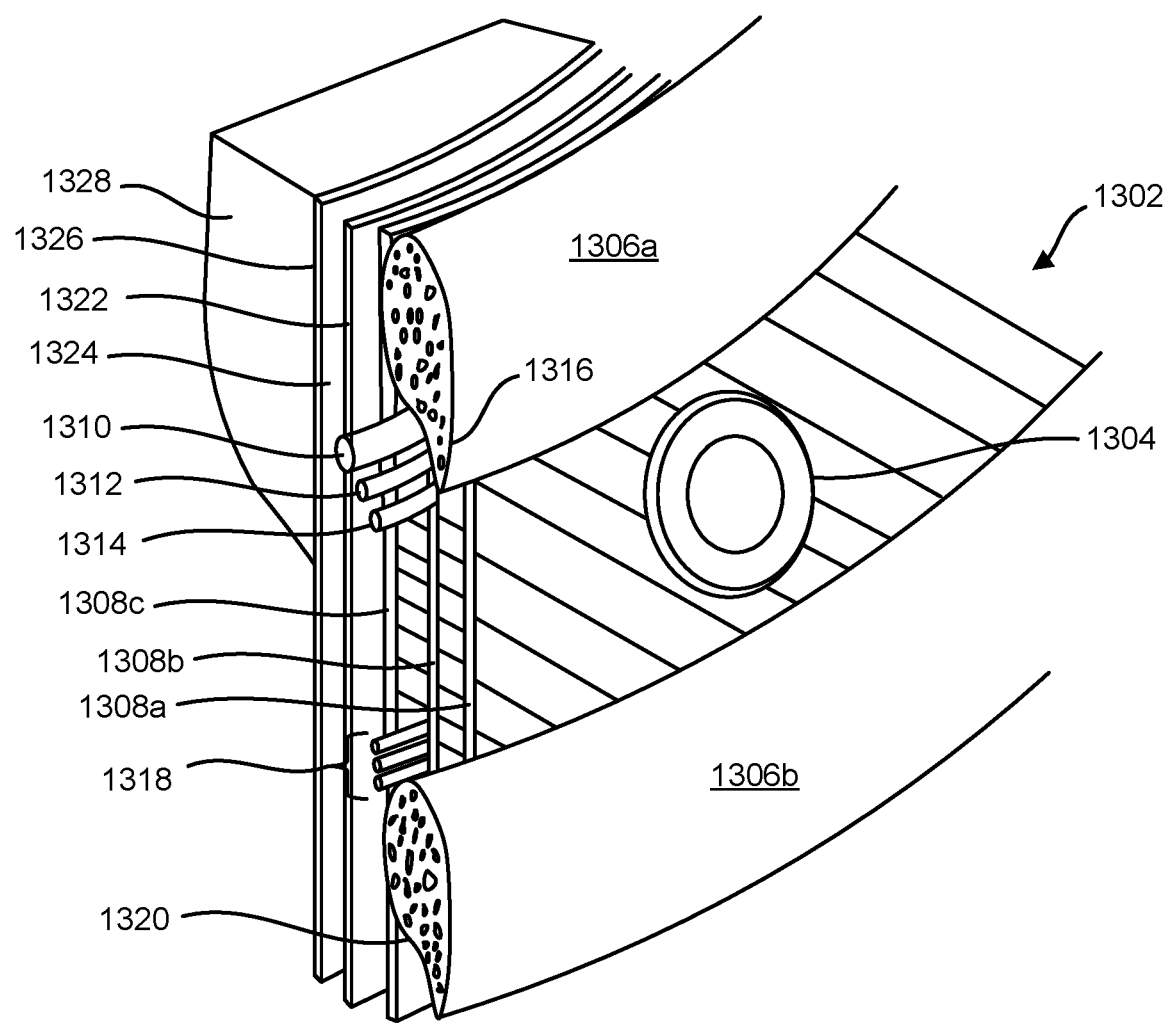
FIG. 13 is an illustration of an intercostal space associated with the cardiac notch of the left lung with an exemplary lead fixation receptacle having features consistent with the current subject matter inserted therein.

FIG. 13 is an illustration 1300 of an intercostal space 1302 associated with the cardiac notch of the left lung with an exemplary lead receptacle 1304 having features consistent with the present disclosure. Lead receptacle 1304 can facilitate the placement of leads, and/or other instruments and avoid the leads and/or instruments physically contacting the intercostal tissue. When the distal end of the lead is positioned to terminate in the intercostal muscle, the lead can be passed through lead receptacle 1304 that has been previously placed within the patient's intercostal muscles. Lead receptacle 1304 can be configured to be electrically insulated so that electrical energy emanating from the lead will not stimulate the surrounding intercostal and skeletal muscle tissue, but will allow the electrical energy to traverse through and stimulate cardiac tissue.

The intercostal space 1302 is the space between two ribs, for example, rib 1306a and rib 1306b. Intercostal muscles 1308a, 1308b and 1308c can extend between two ribs 1306a and 1306b, filling intercostal space 1302. Various blood vessels and nerves can run between the different layers of intercostal muscles. For example, intercostal vein 1310, intercostal artery 1312, the intercostal nerve 1314 can be disposed under a flange 1316 of upper rib 1306a and between the innermost intercostal muscle 1308c and its adjacent intercostal muscle 1308b. Similarly, collateral branches 1318 can be disposed between the innermost intercostal muscle 1308c and its adjacent intercostal muscle 1308b.

The endothoracic facia 1320 can abut the inner-most intercostal muscle 1308c and separate the intercostal muscles from the parietal pleura 1322. The pleural cavity 1324 can be disposed between the parital pleura 1322 and the visceral pleura 1326. The visceral pleura 1326 can abut the lung 1328.

Figure 14:
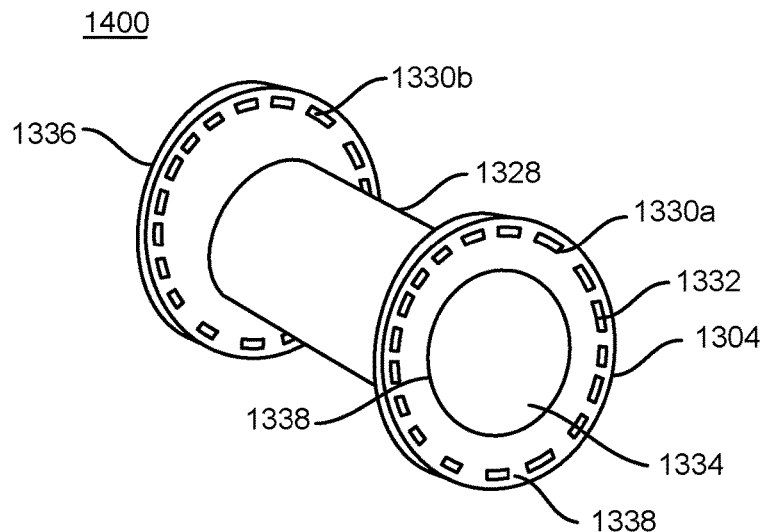
FIG. 14 is an illustration of an exemplary lead fixation receptacle having features consistent with the current subject matter.

FIG. 14 is an illustration 1400 of an exemplary lead fixation receptacle 1304 illustrated in FIG. 13, having features consistent with the present disclosure.

Lead receptacle 1304 may comprise a cylindrical body, or lumen 1328, from an outer side of an outermost intercostal muscle to an inner side of an innermost intercostal muscle of an intercostal space. Lumen 1328 may be configured to support a lead traversing through it. Lumen 1328 may comprise an electrically insulating material configured to inhibit traversal of electrical signals through walls of lumen 1328. In some variations, end 1336 of the receptacle 1304 may pass through the innermost intercostal muscle 1308c. In some variations, end 1338 of receptacle 1304 can pass through outermost intercostal muscle 1308a.

Lumen 1328 can terminate adjacent the pleural space 1324. In some variations, the lumen 1328 can terminate in the mediastinum. In some variations, receptacle 1304 can be configured to be screwed into the intercostal muscles 1308a, 1308b, and 1308c. Receptacle 1304 can also be configured to be pushed into the intercostal muscles 1308a, 1308b and 1308c.

Lead receptacle 1304 may include a fixation flange 1330a. Fixation flange 1330a may be disposed on the proximal end of the lumen 1328 and configured to abut the outermost intercostal muscle 1308a. Lead receptacle 1304 may include a fixation flange 1330b. Fixation flange 1330b can be disposed on the distal end of the lumen 1328 and configured to abut the outermost intercostal muscle 1308c. Lead receptacle 1304 can be implanted into the intercostal muscles 1308a, 1308b, and 1308c by making an incision in the intercostal muscles 1308a, 1308b, and 1308c, stretching the opening and positioning lead receptacle 1304 into the incision, taking care to ensure that the incision remains smaller than the outer diameter of flanges 1330a and 1330b. In some variations flanges 1330a and 1330b can be configured to be retractable allowing for removal and replacement of the lead fixation receptacle 1304.

Lead receptacle 1304 can be fixed in place by using just flanges 1330a and 1330b. Lead receptacle 1304 may also be fixed in place by using a plurality of surgical thread eyelets 1332. Surgical thread eyelets 1332 can be configured to facilitate stitching lead receptacle 1304 to the intercostal muscles 1308a and 1308c to fix lead receptacle 1304 in place.

Receptacle 1304 can include an internal passage 1334. Internal passage 1334 can be configured to receive one or more leads and facilitate their traversal through the intercostal space 1302.

Lead receptacle 1304 can be formed from an electrically insulating material. The electrically insulating material can electrically isolate the intercostal muscles 1308a, 1308b and 1308c from the leads traversing through lead receptacle 1304.

Lead receptacle 1304 can be formed from materials that are insulative. The material can include certain pharmacological agents. For example, antibiotic agents, immunosuppressive agents to avoid rejection of lead receptacle 1304 after implantation, and the like. In some variations, lead receptacle 1304 can be comprised of an insulative polymer coated or infused with an analgesic. In some variations, the lead receptacle 1304 can be comprised of an insulative polymer coated or infused with an anti-inflammatory agent. The polymer can be coated or infused with other pharmacological agents known to one skilled in the art to treat acute adverse effects from the implantation procedure or chronic adverse effects from the chronic implantation of the lead or receptacle within the thoracic cavity.

Figure 15:
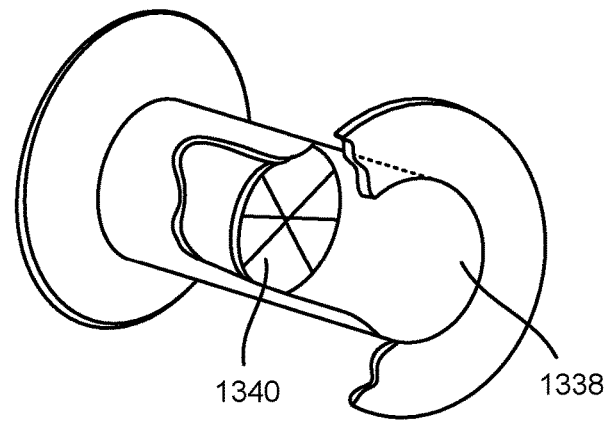
FIG. 15 is an illustration of an exemplary lead fixation receptacle having features consistent with the current subject matter; and, FIG. 16 is an illustration of an exemplary lead fixation receptacle having features consistent with the current subject matter.

FIG. 15 is an illustration of lead receptacle 1304 having features consistent with the present disclosure. Lead fixation receptacle can comprise a septum 1340, or multiple septums disposed traversely within lumen 1338. Septum 1340 can be selectively permeable such that when a lead is inserted through septum 1340, septum 1340 can be configured to form a seal around the lead traversing through lumen 1338 to prevent the ingress or egress of gas, fluid, other materials, and the like, through lumen 1338. Septum 1340 may optionally permit the egress of certain gas and fluid but prevent ingress of such materials through lumen 1338.

In some variations, the lead receptacle can comprise multiple lumens. For example, lead receptacle can comprise a second lumen configured to traverse from an outermost side of an outermost intercostal muscle to an innermost side of an innermost intercostal muscle. Second lumen can be configured to facilitate dispensing of pharmacological agents into the thorax of the patient.

The lumens for such a lead receptacle can be used for differing purposes in addition to the passage of a single lead into the pleural space or mediastinum. The multiple lumens can provide access for multiple leads to be passed into the pleural space or mediastinum.

Figure 16:
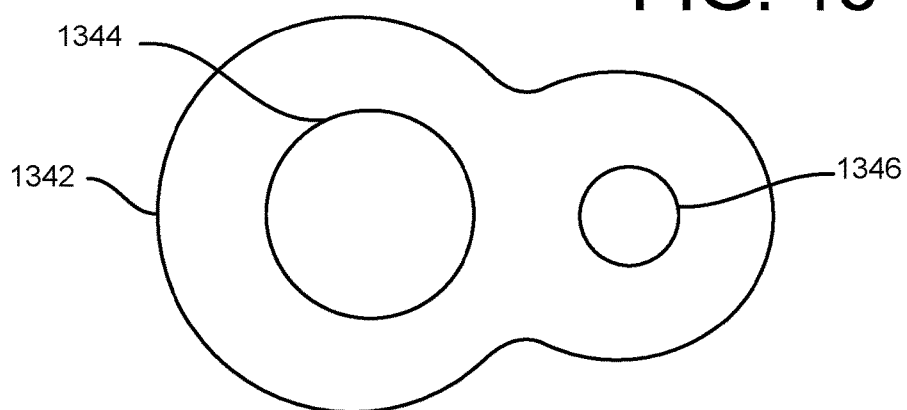

FIG. 16 is an illustration of an exemplary lead fixation receptacle 1342 having features consistent with the present disclosure. Lead fixation receptacle 1342 can include a first lumen 1344, similar to lumen 1338 of the lead receptacle 1304 illustrated in FIGS. 14 and 15. Lead fixation receptacle 1342 can include an additional lumen 1346. Additional lumen 1346 can be provided as a port to provide access to the thoracic cavity of the patient. Access can be provided to facilitate dispensing of pharmacological agents, such as pharmacological agents to treat various adverse effects such as infection or pain in the area surrounding lead receptacle 1342, pleural space, mediastinum, and/or other areas surrounding the thoracic cavity of the patient. Additional lumen 1346 can provide access for treatment of other diseases or disorders affecting organs or other anatomical elements within the thoracic cavity. For example, additional lumen 1346 can facilitate the evacuation of gas or fluid from the thorax, and the like.

The lead receptacle as described with reference to FIGS. 13-16 can be fixated to cartilage, or bone within the thoracic cavity. In some variations, the lead receptacle can be configured to be disposed between the intercostal muscles and a rib, thereby potentially reducing damage to the intercostal muscles caused by its insertion. The lead receptacle can be in passive contact with tissue surrounding the cardiac notch. For example, the lead receptacle can abut the superficial facia on the outermost side and the endothoracic facia or the parietal pleura on the innermost side.

In some variations, the lead receptacle can be actively fixed into position using one end of the lead receptacle. For example, only one flange can include surgical thread holes to facilitate sewing of the flange into the intercostal muscles.

Active fixation, whether at flanges, or along the lumen of the lead fixation receptacle, can include, for example, the use of tines, hooks, springs, screws, flared wings, flanges and the like. Screws can be used to screw the lead fixation receptacle into bone or more solid tissues within the thoracic cavity. Hooks, tines, springs, and the like, can be used to fix the lead fixation receptacle into soft tissues within the thoracic cavity.

In some variations the lead receptacle can be configured to facilitate in-growth of tissue into the material of which the lead fixation receptacle is comprised. For example, the lead fixation receptacle can be configured such that bone, cartilage, intercostal muscle tissue, or the like, can readily grow into pockets or fissures within the surface of the lead receptacle. Facilitating the growth of tissue into the material of the lead receptacle can facilitate fixation of the receptacle.

In some variations, the receptacle can be configured to actively fix between layers of the intercostal muscle. With reference to FIG. 13, the layered nature of the intercostal muscle layers 1308a, 1308b and 1308c can be used to facilitate fixation of the lead receptacle into the intercostal space. For example, flanges can be provided that extend between the intercostal muscle layers. Incisions can be made at off-set positions at each layer of intercostal muscle such that when the lead receptacle is inserted through the incisions, the intercostal muscles apply a transverse pressure to the lead receptacle keeping it in place. For example, a first incision can be made in the first intercostal muscle layer 1308a, a second incision can be made in the second intercostal muscle layer 1308b, offset from the first incision, and a third incision can be made to the third intercostal muscle layer 1308c in-line with the first incision. Inserting the lead receptacle through the incisions, such that the lead receptacle is situated through all three incisions, will cause the second intercostal muscle layer 1308b to apply a transverse pressure to the lead receptacle that is countered by the first intercostal muscle layer 1308a and the third intercostal muscle layer 1308c, facilitating keeping the lead receptacle in place.

Sensing and detection will be performed using one or more available signals to determine when pacing should be delivered or inhibited. Cardiac signals will be measured from one or more electrodes. Additional non-cardiac sensors may also be used to enhance the accuracy of sensing and detection. Such sensors include, but are not limited to rate response sensors, posture/positional sensors, motion/vibration sensors, myopotential sensors and exogenous noise sensors. One or more algorithms will be utilized to make decisions about pacing delivery and inhibition. Such algorithms will evaluate available signal attributes and relationships, including but not limited to analysis of morphology, timing, signal combinations, signal correlation, template matching or pattern recognition.

A pulse generator, such as pulse generator 102 illustrated in FIG. 1, can be configured to monitor physiological characteristics and physical movements of the patient. Monitoring can be accomplished through sensors disposed on, or in, the pulse generator, and/or through sensors disposed on one or more leads disposed within the body of the patient. The pulse generator can be configured to monitor physiological characteristics and physical movements of the patient to properly detect heart arrhythmias, dyssynchrony, and the like.

Sensor(s) can be configured to detect an activity of the patient. Such activity sensors can be contained within or on the housing of the pulse generator, such as pulse generator 102 illustrated in FIG. 1. Activity sensors can comprise one or more accelerometers, gyroscopes, position sensors, and/or other sensors, such as location-based technology, and the like. Sensor information measured by the activity sensors can be cross-checked with activity information measured by any concomitant devices.

In some variations, an activity sensor can include an accelerometer. The accelerometer can be configured to detect accelerations in any direction in space. Acceleration information can be used to identify potential noise in signals detected by other sensor(s), such as sensor(s) configured to monitor the physiological characteristics of the patient, and the like, and/or confirm the detection of signals indicating physiological issues, such as arrhythmias or other patient conditions.

In some variations, a lead, such as lead 802 in FIG. 8, can be configured to include sensors that are purposed solely for monitoring the patient's activity. Such sensors may not be configured to provide additional assistance during the implantation procedure. These sensors can include pulmonary, respiratory, minute ventilation, accelerometer, hemodynamic, and/or other sensors. Those sensors known in the art that are used to real-time, or periodically monitor a patient's cardiac activity can be provided in the leads. These sensors are purposed to allow the implanted device to sense, record and in certain instances, communicate the sensed data from these sensors to the patient's physician. In alternative embodiments, the implanted medical device may alter the programmed therapy regimen of the implanted medical device based upon the activity from the sensors.

In some variations, sensors, such as sensors 810 and 812 of FIG. 8A, may be configured to detect the condition of various organs and/or systems of the patient. Sensor(s) 810, 812 can be configured to detect movement of the patient to discount false readings from the various organs and/or systems. Sensor(s) 810, 812 can be configured to monitor patient activity. Having a distal end 806 of lead 802 positioned in the cardiac notch abutting the parietal pleura, sensor(s) 810, 812 can collect information associated with the organs and/or systems of the patient in that area, for example the lungs, the heart, esophagus, arteries, veins and other organs and/or systems. Sensor(s) 810 can include sensors to detect cardiac ECG, pulmonary function, sensors to detect respiratory function, sensors to determine minute ventilation, hemodynamic sensors and/or other sensors. Sensors can be configured independently to monitor several organs or systems and/or configured to monitor several characteristics of a single organ simultaneously. For example, using a first sensor pair, the implanted cardiac pacing system may be configured to monitor the cardiac ECG signal from the atria, while simultaneously, a second sensor pair is configured to monitor the cardiac ECG signal from the ventricles.

A lead disposed in the body of a patient, such as lead 802 of FIG. 8A, can include sensors at other areas along the lead, for example, sensors 812. The location of sensors 812 along lead 802 can be chosen based on proximity to organs, systems, and/or other physiological elements of the patient. The location of sensors 812 can be chosen based on proximity to other elements of the implanted cardiac pacing system.

Additional leads may be used to facilitate an increase in the sensing capabilities of the implantable medical device. In one embodiment, in addition to at least one lead disposed within the intercostal muscle, pleural space or mediastinum, another lead is positioned subcutaneously and electrically connected to the implantable medical device. The subcutaneously placed lead can be configured to enhance the implantable medical device's ability to sense and analyze far-field signal's emitted by the patient's heart. In particular, the subcutaneous lead enhances the implantable medical device's ability to distinguish signals from particular chambers of the heart, and therefore, appropriately coordinate the timing of the required pacing therapy delivered by the implantable medical device.

Additional leads in communication with the implantable medical device or pulse generator, and/or computing device, can be placed in other areas within the thoracic cavity in order to enhance the sensing activity of the heart, and to better coordinate the timing of the required pacing therapy delivered by the implantable medical device. In certain embodiments, these additional leads are physically attached to the implantable medical device of the present disclosure.

The leads used to deliver therapeutic electrical pulses to pace the heart can comprise multiple poles. Each pole of the lead can be configured to deliver therapeutic electrical pulses and/or obtain sensing information. The different leads can be configured to provide different therapies and/or obtain different sensing information. Having multiple sensors at multiple locations can increase the sensitivity and effectiveness of the provided therapy.

Figure 8B:
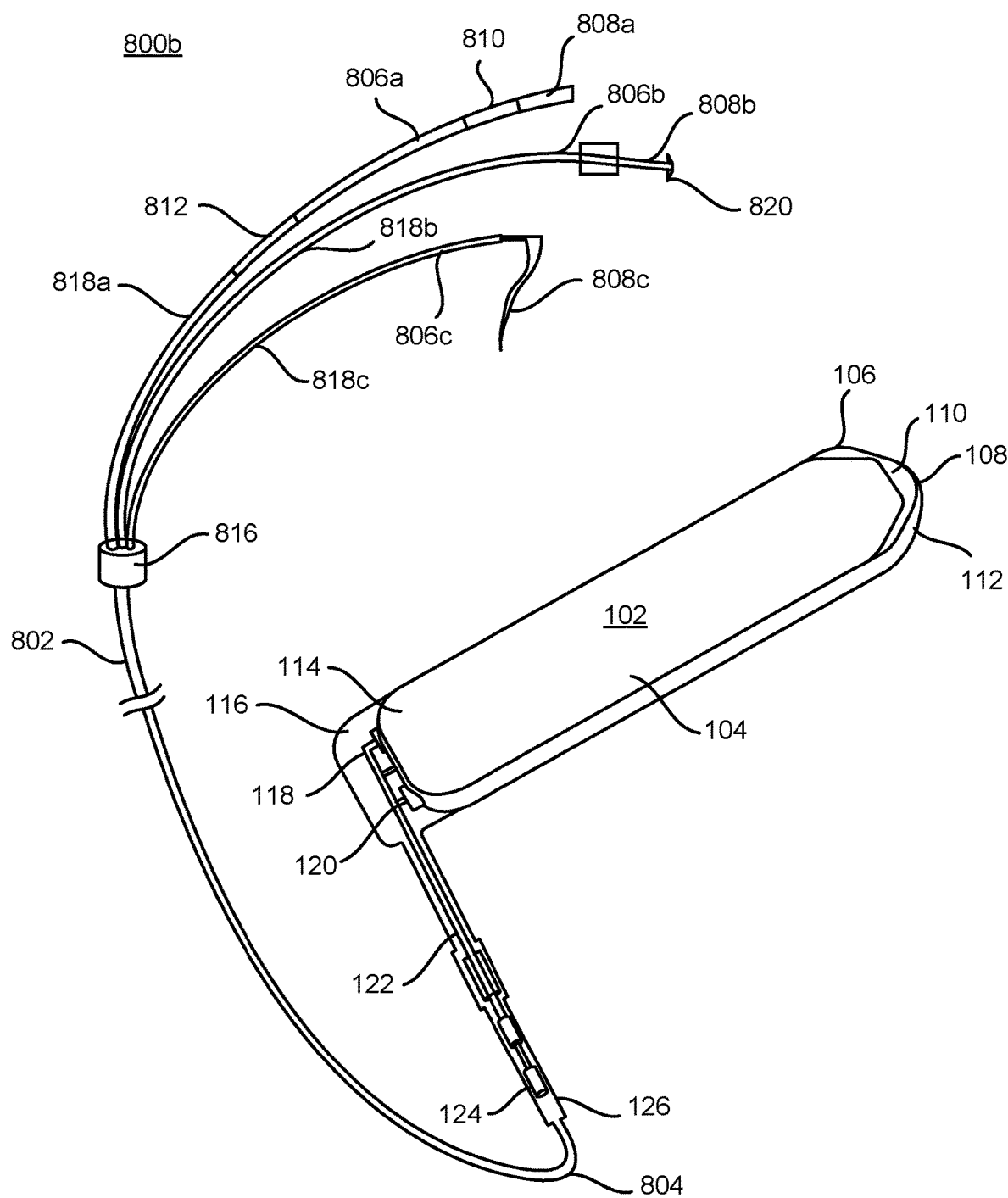
FIG. 8B is an illustration of an exemplary lead having features consistent with the current subject matter.

FIG. 8B is an illustration 800b of an exemplary lead 802 having features consistent with the present disclosure. In some variations, lead 802 can comprise a yoke 816. The yoke can be configured to maintain a hermetically sealed housing for the internal electrical cables of lead 802, while facilitating splitting of the internal electrical cables into separate end-leads 818a, 818b, 818c. Yoke 816 can be disposed toward distal end of lead 802. While three end-leads 818a, 818b, 818c are illustrated in FIG. 8B, the current disclosure contemplates fewer end-leads as well as a greater number of end-leads emanating from yoke 816.

The different end-leads 818a, 818b, 818c, can include different electrodes and/or sensors. For example, end-lead 818b can include an electrode 808b at the distal end 806b of end-lead 818b that differs from electrode 808a at distal end 806a of end-lead 818a. Electrode 808b can have flanges 820. Flanges 820 can be configured to act as an anchor, securing the distal end 806b of end-lead 818b in position within the patient. Electrode 808b with flanges 820 can be suitable for anchoring into high-motion areas of the body where end-lead 818b would otherwise move away from the desired location without the anchoring effect provided by flanges 820. Similarly, electrode 808c at the distal end 806c of end-lead 818c can be configured for a different function compared to the electrodes at the end of other end-leads.

Lead 802 can be a multi-pole lead. Each pole can be electronically isolated from the other poles. The lead 802 can include multiple isolated poles, or electrodes, along its length. The individual poles can be selectively activated. The poles may include sensors for monitoring cardiac or other physiological conditions of the patient, or electrodes for deliver therapy to the patient.

The sensing characteristics of a patient can change over time, or can change based on a patient's posture, a multi-pole lead permits the implantable medical device facilitate monitoring a patient's state through multiple sensing devices, without requiring intervention to reposition a lead. Furthermore, a multi-pole lead can be configured to facilitate supplementary sensing and therapy delivery vectors, such as sensing or stimulating from one pole to a plurality of poles, sensing or stimulating from a plurality of poles to a single pole, or sensing or stimulating between a plurality of poles to a separate plurality of poles. For example, should one particular vector be ineffective at treating a particular arrhythmia, the implantable medical device, or pulse generator, can be configured to switch vectors between the poles on the lead and reattempt therapy delivery using this alternative vector. This vector switching is applicable for sensing. Sensing characteristics can be monitored, and if a sensing vector becomes ineffective at providing adequate sensing signals, the implantable medical device can be configured to switch vectors or use a combination of one or more sensor pairs to create a new sensing signal.

In some variations, at yoke 816, each of the poles of the multi-pole lead can be split into their separate poles. Each of the end-leads emanating from the yoke 816 can be associated with a different pole of the multi-pole lead.

Some of the end-leads emanating from yoke 816 can be configured for providing sensor capabilities of and/or therapeutic capabilities to the patient's heart. Others of the end-leads emanating from yoke 816 can be configured to provide sensor capabilities and/or therapeutic capabilities that are unrelated to the heart. Similarly, the cardiac pacing system herein described can include leads 802, or medical leads, that provide functionality unrelated to the heart.

In some variations, the lead can be bifurcated. A bifurcated lead can comprise two cores within the same lead. In some variations, the different cores of the bifurcated lead can be biased to bend in a predetermined manner and direction upon reaching a cavity. Such a cavity can, for example, be the mediastinum. Bifurcated lead cores can be comprised of shape memory materials, for example, nitinol or other material known in the art to deflect in a predetermined manner upon certain conditions. The conditions under which the bifurcated lead cores will deflect include electrical stimulation, pressure, temperature, or other conditions. In some variations, each core of the bifurcated lead can be configured so that it is steerable by the physician, or an automated system, to facilitate independent advancement of each core of the bifurcated lead, in different directions.

In some variations, sensors from the cardiac pacing system may be selected to optimize sensing characteristics of the cardiac signals. Sensing signals, comprised from one or more sensor pairs may be selected via manual operation of the programming system or automatic operation of the implanted cardiac pacing system. Sensing signals may be evaluated using one of several characteristics including signal amplitude, frequency, width, morphology, signal-to-noise ratio, and the like.

The cardiac pacing system can be configured to use multiple sensors to generate one or more input signals, optionally apply filtering of varying levels to these signals, perform some form of verification of acceptance upon the signals, use the signals to measure levels of intrinsic physiological activity to, subsequently, make therapy delivery decisions. Methods to perform such activities in part or in total include hardware, software, and/or firmware based signal filters, signal amplitude/width analysis, timing analysis, morphology analysis, morphological template comparison, signal-to-noise analysis, impedance analysis, acoustic wave and pressure analysis, or the like. The described analyses may be configured manually via the programming system or via automatic processes contained with the operation software of the cardiac pacing system.

While components have been described herein in their individual capacities, it will be readily appreciated the functionality of individually described components can be attributed to one or more other components or can be split into separate components. This disclosure is not intended to be limiting to the exact variations described herein, but is intended to encompass all implementations of the presently described subject matter.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A method of delivering a lead comprising:
advancing into a patient a lead for delivering electrical stimuli to a heart including an accelerometer configured to facilitate delivery of the lead to a desired location within a mediastinum of the patient, proximate the heart but not physically in contact with the heart or pericardium; and
determining a location of a distal end of the lead in the patient utilizing the accelerometer, wherein the location is not in the heart or pericardium.

2. The method of claim 1, wherein the accelerometer is disposed at a distal end of the lead.

3. The method of claim 1, further comprising:
receiving movement information from the accelerometer during advancement of the lead;
wherein the determining of the location of the distal end of the lead utilizes the movement information received from the accelerometer.

4. The method of claim 3, wherein the movement information is received continuously during at least a portion of the advancement of the lead.

5. The method of claim 4, further comprising:
determining a continuous path taken by the lead based on the movement information;
wherein the determining the location of the distal end of the lead in the patient utilizes the determined continuous path.

6. The method of claim 1, further comprising:
detecting acoustic pressure waves during the advancing of the lead;
wherein determining the location of the distal end of the lead includes comparing the detected acoustic pressure waves with a known model.

7. The method of claim 6, wherein the acoustic pressure waves are generated by an anatomical structure of the patient.

8. The method of claim 6, wherein the anatomical structure of the patient comprises a blood-filled vessel.

9. The method of claim 6, wherein the anatomical structure of the patient is a heart.

10. The method of claim 1, further comprising:
generating artificial pressure waves in the patient in a controlled manner;
detecting the artificial pressure waves with the accelerometer;
wherein the determining of the location of the distal end of the lead includes comparing the detected artificial pressure waves with a known model.

11. A cardiac pacing system comprising:
a lead configured to electrically couple with a pulse generator and to transmit therapeutic electric pulses to a patient, the at least one lead comprising:
at least one accelerometer disposed on the lead and configured to facilitate delivery of the lead to a desired location within a mediastinum of the patient, proximate the heart but not physically in contact with the heart or pericardium;
at least one programmable processor; and
a non-transitory machine-readable medium storing instructions which, when executed by the at least one programmable processor, cause the at least one programmable processor to perform operations comprising:
determining a location of a distal end of the lead in the patient utilizing the accelerometer, wherein the location is not in the heart or pericardium.

12. The cardiac pacing system of claim 11, wherein the accelerometer is disposed at a distal end of the lead.

13. The cardiac pacing system of claim 11, wherein the accelerometer is configured to transmit movement information during advancement of the lead; and
wherein the cardiac pacing system is configured to determine the location of the distal end of the lead utilizing movement information transmitted by the accelerometer.

14. The cardiac pacing system of claim 13, wherein the accelerometer is configured to continuously transmit during at least a portion of the advancement of the lead.

15. The cardiac pacing system of claim 14, wherein the system is configured to determine a continuous path taken by the lead based on the movement information; and
wherein determining the location of the distal end of the lead utilizes the continuous path.

16. The cardiac pacing system of claim 11, wherein the accelerometer is configured to detect acoustic pressure waves during delivery of the lead; and
wherein the system is configured to determine the location of the distal end of the lead at least by comparing the detected acoustic pressure waves with a known model.

17. The cardiac pacing system of claim 16, wherein the acoustic pressure waves are generated by an anatomical structure of the patient.

18. The cardiac pacing system of claim 17, wherein the anatomical structure of the patient comprises a blood-filled vessel.

19. The cardiac pacing system of claim 17, wherein the anatomical structure of the patient is a heart.

20. The cardiac pacing system of claim 11, wherein the accelerometer is configured to detect artificial pressure waves generated in a controlled manner in the patient, and
wherein the cardiac pacing system is configured to determine the location of the distal end of the lead at least by comparing the detected artificial pressure waves with a known model.

* * * * *